(12) United States Patent
Dotan et al.

(10) Patent No.: US 7,592,150 B2
(45) Date of Patent: *Sep. 22, 2009

(54) METHOD FOR DIAGNOSING DISEASES BASED ON LEVELS OF ANTI-GLYCAN ANTIBODIES

(75) Inventors: Nir Dotan, Rehovot (IL); Avinoam Dukler, Moddi'in (IL)

(73) Assignee: Glycominds, Ltd (IL)

( * ) Notice: Subject to any disclaimer, the term of this patent is extended or adjusted under 35 U.S.C. 154(b) by 412 days.

This patent is subject to a terminal disclaimer.

(21) Appl. No.: 10/728,227

(22) Filed: Dec. 3, 2003

(65) Prior Publication Data

US 2005/0124006 A1 Jun. 9, 2005

(51) Int. Cl.
*G01N 33/53* (2006.01)
*G01N 33/543* (2006.01)
*G01N 33/567* (2006.01)

(52) U.S. Cl. ............... 435/7.95; 435/7.1; 435/7.24; 435/7.31; 435/7.92; 435/40.5; 435/255.2; 435/287.2; 435/942; 436/503; 436/513; 436/518; 436/172; 436/811

(58) Field of Classification Search ............ 435/7.1, 435/7.24, 7.31, 7.92, 7.95, 40.5, 255.2, 287.2, 435/942; 436/503, 513, 518, 172, 811
See application file for complete search history.

(56) References Cited

U.S. PATENT DOCUMENTS

| | | | |
|---|---|---|---|
| 5,443,952 A * | 8/1995 | Pestronk | 435/7.1 |
| 5,932,429 A | 8/1999 | Targan et al. | 435/7.24 |
| 6,033,864 A | 3/2000 | Braun et al. | 435/7.1 |
| 6,074,835 A | 6/2000 | Braun et al. | 435/7.211 |
| 6,218,129 B1 | 4/2001 | Walsh et al. | 435/7.21 |
| 6,294,321 B1 * | 9/2001 | Wakshull et al. | 435/4 |
| 7,109,182 B2 * | 9/2006 | Esnault et al. | 514/61 |
| 2003/0143649 A1 | 7/2003 | Boone et al. | 435/7.31 |

FOREIGN PATENT DOCUMENTS

| | | |
|---|---|---|
| WO | WO 92/16837 | 10/1992 |
| WO | WO 00/49412 | 8/2000 |
| WO | WO 01/40796 | 6/2001 |
| WO | WO 02/064556 A2 | 8/2002 |
| WO | WO 2004/015420 A1 | 2/2004 |

OTHER PUBLICATIONS

Main et al., 1988. Antibody to *Saccharomyces cerevisiae* (baker's yeast) in Crohn's disease. British Medical Journal 297: 1105-1106.*
Quinton et al., 1998. Anti-*Saccharomyces cerevisiae* mannan antibodies combined with antineutrophil cytoplasmic autoantibodies in inflammatory bowel disease: prevalence and diagnostic role. Gut 42: 788-791.*
Krause et al., 2002. Anti-*Saccharomyces cerevisiae* antibodies—a novel serologic marker for Behcet's disease. Clinical and Experimental Rheumatology 20 (Suppl. 26): S21-S24.*
Schwarz et al. *Glycobiol.*, 13(11):749-754 (2003).
Sendid et al. *Clin. Diagnostic Lab. Immunol.*, 3(2):219-226 (1996).
Wang et al. *Proteomics*, 3:2167-2175 (2003).
International Search Report and Written Opinion for PCT/IB2004/004389, mailed Jul. 29, 2005.
Banin et al. *Trends Glycosci. Glycotechnol.*, 14(77):127-137 (2002).
Bao *J. Chromatogr. B.*, 699(1+2):463-480 (1997).
Broekroelofs et al. *Dig. Dis. Sci.*, 39(3):545-549 (1994).
Cambridge et al. *Gut*, 33(5):668-674 (1994).
Hou et al. *J. Immunol.*, 170:4373-4379 (2003).
Pool et al. *Gut*, 34(1):46-50 (1993).
Rongen et al. *J. Immunol. Meth.*, 204:105-133 (1997).
Saxon et al. *J. Allergy Clin. Immunol.*, 86(2):202-210 (1990).

* cited by examiner

*Primary Examiner*—Ann Y Lam
*Assistant Examiner*—James L Grun
(74) *Attorney, Agent, or Firm*—Mintz, Levin, Cohn, Ferris, Glovsky and Popeo PC; Ivor R. Elrifi; Ingrid A. Beattie

(57) ABSTRACT

Disclosed are methods for diagnosing Crohn's disease (CD) or anti-phospholipid syndrome by measuring levels of antibodies to glycans in a biological sample.

54 Claims, 3 Drawing Sheets

METHOD FOR DIAGNOSING DISEASES BASED ON LEVELS OF ANTI-GLYCAN ANTIBODIES

FIELD OF THE INVENTION

The invention relates generally to a method for diagnosing diseases by detecting levels of anti-bodies to glycans in a subject. More particularly, the invention relates to methods for diagnosing Crohn's disease (CD) or anti-phospholipid syndrome (APS).

BACKGROUND OF THE INVENTION

Inflammatory bowel disease (IBD), which occurs worldwide and afflicts millions of people, is the collective term used to describe two gastrointestinal disorders of unknown etiology: Crohn's disease (CD) and ulcerative colitis (UC). IBD and irritable bowel syndrome (IBS) will affect one-half of all Americans during their lifetime, at a cost of several billion dollars. A primary determinant of these high medical costs is the difficulty of diagnosing digestive diseases. The cost associated with IBD and IBS is compounded by lost productivity, with persons suffering from these disorders missing at least 8 more days of work annually than the national average.

Symptoms associated with Crohn's disease include, e.g., abdominal pain, chronic diarrhea, rectal bleeding, weight loss and cramping. These symptoms are also found in common with irritable bowel syndrome and other inflammatory bowel diseases. This makes definitive diagnosis of CD extremely difficult. In fact, only about one-tenth of the several million people suspected of suffering from CD are actually diagnosed with the disease The difficulty in differentially diagnosing CD from other digestive diseases like UC and IBS hampers early and effective treatment of these diseases.

Crohn's disease (ileitis regionalis or ileitis terminalis) may affect any part of the gut with the ileum and colon as the most commonly affected sites. In CD the inflammation is asymmetrical and segmental, with areas of both healthy and diseased tissue. By contrast, ulcerative colitis (hemorrhagic idiopathic proctocolitis) is characterized by symmetrical inflammation-restricted to mucosa and submucosa—ascending uninterrupted from rectum to colon.

Crohn's disease is typically diagnosed using upper or lower GI endoscopy and/or by X-ray examination of the small intestine including ileum. In CD no typical endoscopic picture is shown, while in UC the typical pattern detected is an inflamed red mucosal with bleeding. In CD biopsy specimens reveal transmural inflammation with lymphocytes, macrophages and plasma cells while mucosal/submucosal inflammation with granulocytes, eosinophiles and plasma cells are typical findings in UC.

Antiphospholipid syndrome (APS) is characterized by venous or arterial thrombosis, recurrent miscarriages, and thrombocytopenia, which is a low number of blood platelets that can lead to bleeding, seen as bruising and tiny red dots on the skin. Patients with APS also may experience symptoms of stroke such as transient ischemic attacks (TIAs).

Antiphospholipid syndrome is typically diagnosed based on these clinical manifestations and on laboratory test results. A blood sample is analyzed for the presence of antibodies that react with naturally occurring proteins complexed with phospholipids. These are called antiphospholipid antibodies or anticardiolipin antibodies (cardiolipin is one type of phospholipid used in lab tests). Sometimes these antibodies are called lupus anticoagulants when clotting assays are used for their detection.

SUMMARY OF THE INVENTION

The invention is based in part on the discovery that patients with Crohn's disease (CD) or anti-phospholipid syndrome (APS) have elevated serum levels of certain IgG, IgA, and IgM isotype antibodies specific for certain glycan structures, as compared to as compared to the serum levels of these antibodies in healthy individuals or in individuals with other types of gastrointestinal diseases.

Among the advantages of the invention is a highly sensitive serological testing method for definitively distinguishing CD from other digestive diseases. The highly sensitive primary screening assays according to the invention provide physicians with an inexpensive assay for rapidly distinguishing individuals with CD from non diseased individuals, or individuals having UC or IBS. This facilitates earlier and more appropriate therapeutic intervention and minimizing uncertainty for patients and their families.

In one aspect, the invention provides a method of diagnosing Crohn's disease in a subject by providing a test sample from the subject and detecting in the test sample at least one of the following anti-glycan antibodies: anti-Glc ($\beta$) antibody, an anti-Glc (p 1-4) Glc ($\beta$) antibody, an anti-Glc ($\beta$ 1-3) Glc ($\beta$) antibody, an anti-GlcNAc 6-sulfate ($\beta$) antibody an anti-Dextran antibody, an anti-Xylan antibody, an anti-GlcNAc ($\beta$ 1-4) GlcNAc ($\beta$) antibody, an anti-Gal 3 sulphate ($\beta$) antibody, an anti-GlcNAc ($\beta$ 1-3) GalNAc ($\beta$) antibody, an anti-GlcNAc ($\beta$ 1-3) Gal ($\beta$ 1-4) Glc ($\beta$) antibody, and an anti-Gal ($\alpha$ 1-3) Gal ($\beta$ 1-4) GlcNAc ($\beta$) antibody. The presence of one or more of the antibodies in the test sample indicates the subject has Crohn's disease.

In some embodiments, levels of the anti-glycan antibody or antibodies in the test sample are compared to the levels of anti-glycan antibodies in a control sample. The control sample is chosen from a group that includes one or more individuals known to have or not to have a gastrointestinal disorder, or to have or not to have a gastrointestinal disorder other than Crohn's disease. When the control sample is from an individual or individuals that do not have Crohn's disease, or has a gastrointestinal disease other than Crohn's disease, elevated levels in the test sample relative to the control sample indicates that the subject has Crohn's disease.

In some embodiments, the control sample is from one or more individuals with a gastrointestinal disorder that is irritable bowel syndrome or ulcerative colitis or other digestive diseases. In some embodiments, the control sample is from one or more individuals that do not have a gastrointestinal disorder.

In various embodiments, at least 2, 3, 4, 5, 6, or all of these antibodies are detected.

In some embodiments, the method further includes determining whether the test sample has an anti-Mannan antibody, which is also known as an anti-*Saccharomyces cerevisiae* antibody (ASCA). The presence of the anti-Mannan antibody in the sample indicates the subject has Crohn's Disease.

In some embodiments, the method further includes determining whether the test sample has an anti-neutrophil cytoplasmic antibodies (ANCA). The presence of ANCA indicates the subject does not have Crohn's Disease but may have Ulcerative Colitis.

The test sample can be, e.g., a biological fluid. Examples of biological fluids include, e.g., whole blood, serum, plasma, spinal cord fluid, urine, or saliva.

In some embodiments, one, two, three, or all four of an anti-Glc (β 1-3) Glc (β) antibody, anti-Man (α 1-3) Man (α) antibody, anti-Man (α 1-3)[Man (α 1-6)] Man (α) antibodies, and/or anti-Mannan antibodies are detected.

The method can optionally include determining the isotype of the antibody. For example the method can include determining whether the antibody is an IgM, IgA, or IgG-type antibody. In some embodiments, the method is used to identify and compare an anti-Glc (β) IgG antibody, an anti-Glc (β 1-3) Glc (β) IgG antibody, an anti-Glc (β 1-4) Glc (β) IgG antibody, an anti-GlcNAc (β) 6-sulfate IgG antibody, an anti-Man (α) IgG antibody, an anti-Man (α 1-3) [Man (α1-6)] Man (β) IgG antibody, an anti-Man (α 1-3) Man (α) IgG antibody, an anti-Mannan IgG antibody an anti-Mannan IgA antibody, an anti-Xylan IgG antibody, or an anti-Man (α 1-2) Man α IgG antibody.

In some embodiments, a subject is scored as having CD if the test sample has elevated levels of IgG anti-Glc (β 1-3) Glc (β), or IgG anti anti-Man (α 1-3) Man (α), or IgG anti Mannan (ASCA) antibodies, or IgA anti Mannan (ASCA) antibodies, but does not have elevated levels of ANCA.

In some embodiments, a subject is scored as having IBD if the test sample has elevated levels of IgG anti-Glc (β 1-3) Glc (β), or IgG anti anti-Man (α 1-3) Man (α), or IgG anti Mannan (ASCA) antibodies, or IgA anti Mannan (ASCA) antibodies, or ANCA.

In some embodiments, the anti-glycan antibody or antibodies are detected using a fluorescent antibody, or are detected using an enzyme-linked immunoabsorbent assay (ELISA).

The test sample can be, e.g., a biological fluid. Examples of biological fluids include, e.g., whole blood, serum, plasma, spinal cord fluid, urine, or saliva.

The method can optionally include determining the isotype of the antibody. For example the method can include determining whether the antibody is an IgM, IgA, or IgG-type antibody.

Also within the invention are arrays that include reagents (preferably carbohydrate reagents) that specifically detect the CD-detecting antibodies disclosed herein, e.g., an anti-Glc (β) antibody, an anti-Glc (β 1-4) Glc (β) antibody, an anti-Glc (β 1-3) Glc (β) antibody, an anti-GlcNAc 6-sulfate (β) antibody, an anti-Man (α 1-2) Man (α) antibody, an anti-Man (α 1-3) Man (α) antibody, an anti-Man (α 1-6) Man (α) antibody, an anti-Man (α) antibody, an anti-Man (α 1-3)[Man (α 1-6)] Man (α), an anti-Mannan antibody, an anti-Dextran antibody, an anti-Xylan antibody, an anti-GlcNAc (β 1-4) GlcNAc (β) antibody, an anti-Gal 3 sulphate (β) antibody, an anti-aGlcNAc (β 1-3) GalNAc (β) antibody, an anti-GlcNAc (β 1-3) Gal (β 1-4) Glc (β) antibody, or an anti-Gal (α 1-3) Gal (β 1-4) GlcNAc (β) antibody for diagnosing CD.

In some embodiments, the reagents that are used to specifically bind and detect those anti glycans antibodies are the specific glycan structures. In other embodiments, the reagents are other molecules or macromolecules that include the specific glycan structure. For example, the anti-Glc (β 1-3) Glc (β) antibody can be detected using the polysaccharide β-D (1-3) Glucan, a polymer of glucose units connected in a (β, 1-3) glycosidic bond. Thus, the glycan itself can be used for detecting the corresponding antibody or antibodies, as can any carbohydrate, peptide, protein, or any other molecular structure that includes the glycan.

The array may additionally include a reagent or reagent, e.g., a carbohydrate reagent or reagents, that detect an anti-Mannan (ASCA) antibody or a ANCA. In some embodiments, the glycans are attached to the array via a linker. A suitable linker includes at least one ethylene glycol derivative, at least two cyanuric chloride derivatives and an anilino group.

In some embodiment, at least two of the reagent or reagents are provided at the same location on the addressable array.

The invention additionally provides kits that include reagents for detecting anti-glycan antibodies that reveal the presence of Crohn's Disease. The kits includes one or more carbohydrate reagent(s) that specifically reacts with an anti-Glc (β) antibody, an anti-Glc (β 1-4) Glc (β) antibody, an anti-Glc (β 1-3) Glc (β) antibody, an anti-GlcNAc 6-sulfate (β) antibody, an anti-Man (α 1-2) Man (α) antibody, an anti-Man (α 1-3) Man (α) antibody, an anti-Man (α 1-6) Man (α) antibody, an anti-Man (α) antibody, an anti-Man (α 1-3)[Man (α 1-6)] Man (α), an anti-Mannan antibody, an anti-Dextran antibody, an anti-Xylan antibody, an anti-GlcNAc (α 1-4) GlcNAc (β) antibody, an anti-Gal 3 sulphate (β) antibody, an anti-aGlcNAc (β 1-3) GalNAc (β) antibody, an anti-GlcNAc (β 1-3) Gal (β 1-4) Glc (β) antibody, and/or an anti-Gal (α 1-3) Gal (β 1-4) GlcNAc (β) antibody. In some embodiments, the kits contain directions for using the kits to perform the methods described herein. The kits may optionally include reagents for detecting antibody isotypes (e.g., IgA, IgG, and IgM antibodies).

In some embodiments, the kits include reagents that are used to specifically bind and detect those anti glycans antibodies that are the specific glycan structures. In other embodiments, the reagents in the kits are other molecules or macromolecules that include the specific glycan structure. For example, the anti-Glc (β 1-3) Glc (β) antibody can be detected using the polysaccharide β-D (1-3) Glucan, a polymer of glucose units connected in a (β, 1-3) glycosidic bond. Thus, the glycan itself can be used for detecting the corresponding antibody or antibodies, as can any carbohydrate, peptide, protein, or any other molecular structure that includes the glycan.

In some embodiments, the kits include reagents that are used to specifically bind and detect ASCA and/or ANCA.

Also within the invention is a method of diagnosing anti-phospholipid syndrome in a subject by providing a test sample from a subject and detecting in the test sample an anti-chitobiose antibody. Levels of the anti-GlcNAc (β 1-4) GlcNAc (β) antibody in the test sample are compared to the levels of the antibody in a control sample. The control sample is selected from group of one or more individuals known to have or not to have anti-phospholipid syndrome. When the control sample has one or more individuals that to not have APS, an elevated level of anti-GlcNAc (β 1-4) GlcNAc (β) antibodies in the test sample as compared to the control sample indicates the subject has APS.

In some embodiments, the method also includes detecting binding to a β-2 glycoprotein, and comparing the level of binding to the β-2 glycoprotein in the test sample to the level of binding to β-2 glycoprotein in the control sample. Increased binding to the β-2 glycoprotein in the test sample relative to a control sample taken from a non-APS individual or individuals indicates the subject has APS.

The test sample can be, e.g., a biological fluid. Examples of biological fluids include, e.g., whole blood, serum, plasma, spinal cord fluid, urine, or saliva.

The method can optionally include determining the isotype of the antibody. For example the method can include determining whether the antibody is an IgM, IgA, or IgG-type antibody. Also within the invention is an array that includes a reagent (preferably a carbohydrate reagent) that specifically detects and anti-GlcNAc (β 1-4) GlcNAc (β) antibody and (optionally) a reagent that detects a β-2 glycoprotein for detecting APS.

The invention additionally provides kits for diagnosing APS that include reagents for detecting an anti-chitobiose antibody and (optionally) a β-2 glycoprotein. In some embodiments, the kits contain directions for using the kits to perform the methods described herein.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
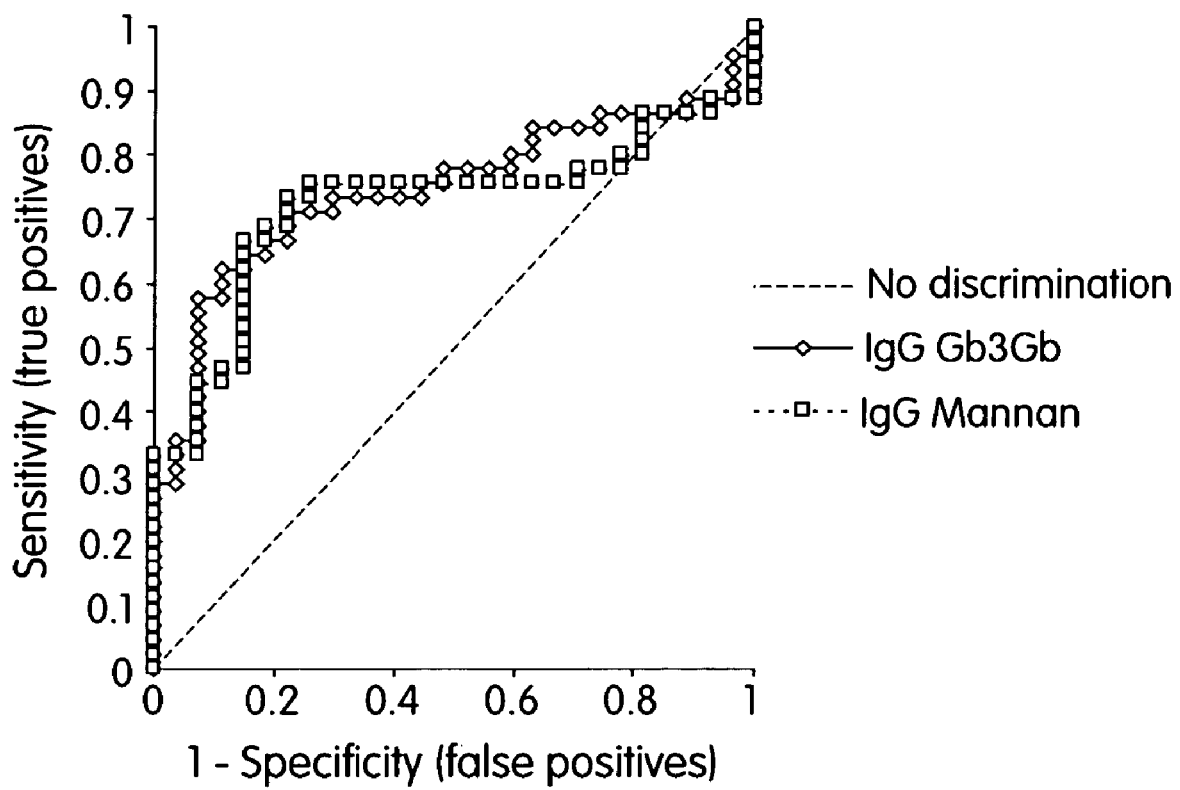
FIG. 1 is a graph showing a Receiver Operator Characteristic (ROC) curve for differentiation between individuals with CD and individuals with other digestive diseases according to different anti glycans antibodies.

Crohn's disease (CD) and anti-phospholipid syndrome (APS) are diagnosed by examining a test sample from a subject for antibodies to one or more specific glycans. The presence of the antibodies in the test sample indicates the subject has CD or APS. In some embodiments, elevated levels of glycans in a test sample from the subject as compared to the levels of the glycan or glycans in a reference sample that does not have CD indicates that the subject has CD. The methods can be used distinguish the presence of CD in a subject from other inflammatory bowel diseases (including ulcerative colitis).

A translation of the LinearCode™ syntax used to describe glycan structure to IUPAC nomenclature can be found in Table 1. The glycans are presented either in the International Union of Pure and Applied Chemistry (IUPAC) condensed form for nomenclature carbohydrate representation or in LINEARCODE® syntax, for linear code syntax principles see (Banin E. Neuberger Y. Altshuler Y. Halevi A. Inbar O. Dotan N. and Dukler A. (2002) A Novel Linear Code Nomenclature for complex Carbohydrates. Trends in Glycoscience and Glycotechnology Vol. 14 No. 77 pp. 127-137). Translation of LINEARCODE® to IUPAC representation is in Table 1. All the glycan structures that discussed in this disclosure, unless mentioned otherwise are connected to in the indicated anomericity α or β to other molecular structure, linker, or solid phase.

As used herein, the term "inflammatory bowel disease" is synonymous with "IBD" and is a collective term referring to both Crohn's disease and ulcerative colitis. Thus, an individual having either Crohn's disease or ulcerative colitis is defined herein as having IBD. Conversely, an individual having neither ulcerative colitis nor Crohn's disease does not have IBD as defined herein. The term "inflammatory bowel disease" distinguishes Crohn's disease and ulcerative colitis from all other disorders, syndromes or abnormalities of the gastroenterological tract including irritable bowel syndrome.

The methods for diagnosing IBD involve determining whether a sample is positive for anti-neutrophil cytoplasmic antibodies (ANCA). Anti-neutrophil cytoplasmic antibodies that produce a perinuclear staining pattern (pANCA) are elevated in 60-80% of UC patients and less frequently in CD and other disorders of the colon. Serum titers of ANCA are elevated in UC patients regardless of clinical status and, thus, do not reflect disease activity. High levels of serum ANCA also persist in UC patients five years post-colectomy. Although pANCA is found only very rarely in healthy adults and children, healthy relatives of UC patients have an increased frequency of pANCA, indicating that pANCA may be an immunogenetic susceptibility marker. ANCA reactivity is also present in a small portion of patients with Crohn's disease. The reported prevalence in CD varies, with most studies reporting that 10 to 30% of CD patients express ANCA (Saxon et al., J. Allergy Clin. Immunol. 86:202-210 (1990); Cambridge et al., Gut 33:668-674 (1992); Pool et al., Gut 3446-50 (1993); and Brokroelofs et al., Dig. Dis. Sci. 39:545-549 (1994)).

As used herein, the term "anti-neutrophil cytoplasmic antibody" is synonymous with "ANCA" and means antibodies to cytoplasmic components of a neutrophil. ANCA, such as serum or saliva ANCA, can be detected using an enzyme-linked immunosorbent assay with alcohol-fixed neutrophils. As disclosed herein, ANCA activity is divided into several broad categories: perinuclear to nuclear staining or cytoplasmic staining with perinuclear highlighting (pANCA); cytoplasmic neutrophil staining without perinuclear highlighting (cANCA); and diffuse staining with speckling across the entire neutrophil (SAPPA). The term ANCA, as used herein, encompasses all varieties of anti-neutrophils cytoplasmic reactivity, including pANCA, cANCA and SAPPA. Similarly, the term "ANCA" encompasses all immunoglobulin isotypes including, for example, immunoglobulin A and G.

The determination of whether a sample is positive for ANCA using non-histological means is made using antigen specific for ANCA using methods described in U.S. Pat. No. 6,218,129. Such an antigen specific for ANCA can be, for example, whole fixed neutrophils; an unpurified or partially purified neutrophil extract; a purified UC pANCA antigen such as a purified protein, protein fragment or synthetically produced peptide; an anti-ANCA idiotypic antibody; or the like. Particularly useful antigens specific for ANCA are peptides, which can be chemically synthesized or expressed on the surface of phage. Purified antigens specific for ANCA can be, for example, histone H1, or an ANCA-reactive fragment of histone H1, as described in U.S. Pat. No. 6,074,835 now U.S. Pat. No. 6,074,835; an ulcerative colitis pANCA secretory vesicle antigen or an ANCA-reactive fragment thereof; or a microbial UC pANCA antigen, such as a histone H1-like antigen, porin antigen, Bacteroides antigen, or ANCA-reactive fragment thereof, as described in U.S. Pat. No. 6,033,864 now U.S. Pat. No. 6,033,864. One skilled in the art understands that additional antigens specific for ANCA, including antigenic fragments and ANCA-reactive peptides, can be identified, for example, using a representative UC pANCA monoclonal antibody.

Generating an Anti-Glycan Antibody Profile

In performing the methods of the invention, a sample to be analyzed is obtained from the subject to be diagnosed. The term "sample," as used herein, means any biological specimen obtained from an individual that contains antibodies. A sample can be, for example, whole blood, plasma, saliva or other bodily fluid or tissue having antibodies, preferably a serum sample. Samples can be diluted if desired before they are analyzed for anti-glycan antibodies. The subject can be, e.g., a human, a non-human primate (including a chimpanzee, ape, gorilla, old world primate), cow, horse, dog, cat, pig, goat, sheep, rodent (including, e.g., a mouse, rat, or guinea pig) Anti-glycan profiles can be determined by using methods known in the art for identifying antibodies to glycans. The methods include those disclosed in e.g., WO00/49412, or WO02/064556, or Schwarz et al., Glycobiology 13:749-54, 2003.

The methods are typically performed using reagents that specifically bind to the anti-glycan antibodies. The reagents can be, e.g., the specific glycan structures. Alternatively, the reagents can be other molecules or macromolecules that include the specific glycan structure. For example, the anti-Glc (β 1-3) Glc (β) antibody can be detected using the polysaccharide β-D (1-3) Glucan, a polymer of glucose units connected in a (β, 1-3) glycosidic bond. Thus, the glycan itself can be used for detecting the corresponding antibody or antibodies, as can any carbohydrate, peptide, protein, or any other molecular structure that includes the glycan.

Glycan antigens used to identify various anti-glycan antibodies can be obtained from a variety of other sources so long as the antigen is capable of binding specifically to the given anti-glycan Binding to anti-glycan antibodies can be performed using variety of other immunoassay formats known in the art, including competitive and non-competitive immunoassay formats can also be used (Self and Cook, Curr. Opin. Biotechnol. 7:60-65 (1996), which is incorporated by reference). Other assays include immunoassays, such as enzyme-linked immunosorbent assays (ELISAs). An enzyme such as horseradish peroxidase (HRP), alkaline phosphatase (AP), β-galactosidase or urease can be linked to a secondary antibody selective for a primary anti-glycan antibody of interest. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-a β-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab')$_2$ anti-human IgG-alkaline phosphatase, for example, can be purchased from Jackson Immuno-Research (West Grove, Pa.).

Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used (Rongen et al., J. Immunol. Methods 204:105-133 (1997)).

A radioimmunoassay can also be used for determining whether a sample is positive for a glycan antibody, or for determining the level of anti-glycan antibodies in a sample. A radioimmunoassay using, for example, an $^{125}$iodine-labeled secondary antibody (Harlow and Lane, Antibodies A Laboratory Manual Cold Spring Harbor Laboratory: New York, 1988, which is incorporated herein by reference) is encompassed within the invention.

A secondary antibody may alternatively be labeled with a chemiluminescent marker. Such a chemiluminescent secondary antibody is convenient for sensitive, non-radioactive detection of anti-glycan antibodies and can be obtained commercially from various sources such as Amersham Lifesciences, Inc. (Arlington Heights, Ill.).

A detectable reagent may also be labeled with a fluorochrome. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of $^{125}$Iodine; or a fluorometer to detect fluorescence in the presence of light of a certain wavelength. For detection of enzyme-linked reagents, a quantitative analysis of the amount of anti-glycan antibodies can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Other methods include, e.g., flow cytometry (including bead based immunoassays), and phage display technology for expressing a recombinant antigen specific for an anti-glycan antibody. Phage particles expressing the antigen specific for a desired anti-glycan antibody can be anchored, if desired, to a multiwell plate using an antibody such as an anti phage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

Anti-glycan antibodies are conveniently performed by simultaneously analyzing multiple samples for CD for the presence of one or more anti-glycan antibodies. For example, the antibodies can be detected using an array of reagents that can bind specifically to the anti glycan antibodies. Preferably, each reagent is provided in a different location with a defined address on the array. By exposing the sample to array all the anti glycan antibodies that bind to the reagent on the array can be detected in one test Suitable arrays that include reagents (preferably carbohydrate reagents) that specifically detect the CD-detecting antibodies disclosed herein, e.g., an anti-Glc (β) antibody, an anti-Glc (β 1-4) Glc (β) antibody, an anti-Glc (β 1-3) Glc (β) antibody, an anti-GlcNAc 6-sulfate (β) antibody, an anti-Man (α 1-2) Man (α) antibody, an anti-Man (α 1-3) Man (α) antibody, an anti-Man (α 1-6) Man (α) antibody, an anti-Man (α) antibody, an anti-Man (α 1-3)[Man (α 1-6)] Man (α), an anti-Manna antibody, an anti-Dextran antibody, an anti-Xylan antibody, an anti-GlcNAc (β1-4) GlcNAc (β) antibody, an anti-Gal 3 sulphate (β) antibody, an anti-aGlcNAc (β 1-3) GalNAc (β) antibody, an anti-GlcNAc (β 1-3) Gal (β1-4) Glc (β) antibody, or an anti-Gal (α 1-3) Gal (β 1-4) GlcNAc (β) antibody for diagnosing CD.

In some embodiments, the reagents that are used to specifically bind and detect those anti glycans antibodies are the specific glycan structures. In other embodiments, the reagents are other molecules or macromolecules that include the specific glycan structure. For example, the anti-Glc (β 1-3) Glc (β) antibody can be detected using the polysaccharide β-D (1-3) Glucan, a polymer of glucose units connected in a (β, 1-3) glycosidic bond. Thus, the glycan itself can be used for detecting the corresponding antibody or antibodies, as can any carbohydrate, peptide, protein, or any other molecular structure that includes the glycan.

The array may additionally include a reagent or reagent, e.g., a carbohydrate reagent or reagents, that detect an anti-Mannan antibodies or a ANCA In some embodiments, the glycans are attached to the array via a linker. A suitable linker includes at least one ethylene glycol derivative, at least two cyanuric chloride derivatives and an anilino group.

Arrays useful for diagnosing APD can include a reagent (preferably a carbohydrate reagent) that specifically detects an anti-chitobiose antibody and, optionally, a reagent that specifically detects a β-2 glycoprotein for detecting.

Interpreting Anti-Glycan Antibody Binding Data

Typically, binding of anti-glycan antibodies to glycans in a sample is compared to a reference population, and differences in levels of the anti-glycan antibodies in the two samples are compared. The threshold for determining whether a test sample is scored positive for CD or APS based on its antglycan antibody profile can be altered depending on the sensitivity or specificity desired. The clinical parameters of sensitivity, specificity, negative predictive value, positive predictive value and overall agreement are calculated using true positives, false positives, false negatives and true negatives. A "true positive" sample is a sample positive for CD according to colonoscopy, radiologic and/or histologic analysis, which is also diagnosed positive according to a method of the invention. A "false positive" sample is a sample negative for CD by colonoscopic, radiologic and/or histologic analysis, which is diagnosed positive according to a method of the invention. Similarly, a "false negative" is a sample positive for CD by colonoscopic, radiologic and/or histologic analysis, which is diagnosed negative according to a method of the invention. A "true negative" is a sample negative for CD by colonoscopic, radiologic and/or histologic analysis, and also negative for CD according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of CD. Sensitivity is calculated as the number of true positive results divided by the sum of the true positives and false negatives. Sensitivity essentially is a measure of how well a method correctly identifies those with disease. In a method of the invention, the anti-glycan antibody values can be selected such that the sensitivity of diagnosing an individual is at least about 60%, and can be, for example, at least about 65%, 70%, 75%, 80%, 85%, 90% or 95%.

As used herein, the term "specificity" means the probability that a method is negative in the absence of CD. Specificity is calculated as the number of true negative results divided by the sum of the true negatives and false positives. Specificity essentially is a measure of how well a method excludes those who do not have CD. The anti-glycan cut-off value can be selected such that, when the sensitivity is at least about 70%, the specificity of diagnosing an individual is in the range of 30-60%, for example, 35-60%, 40-60%, 45-60% or 50-60%.

The term "positive predictive value," as used herein, is synonymous with "PPV" and means the probability that an individual diagnosed as having CD actually has the disease. Positive predictive value can be calculated as the number of true positives divided by the sum of the true positives and false positives. Positive predictive value is determined by the characteristics of the diagnostic method as well as the prevalence of the disease in the population analyzed. In a method of the invention, the anti-glycan antibody cut-off values can be selected such that the positive predictive value of the method in a population having a CD disease prevalence of 15% is at least about 5%, and can be, for example, at least about 8%, 10%, 15%, 20%, 25%, 30% or 40%.

As used herein, the term "overall agreement" means the accuracy with which a method diagnoses a disease state. Overall agreement is calculated as the sum of the true positives and true negatives divided by the total number of sample results and is affected by the prevalence of CD in the population analyzed. The anti-glycan antibody cut-off values can be selected such that the overall agreement of a method of the invention in a patient population having an CD disease prevalence of 15% is at least about 45%, and can be, for example, at least about 50%, 55% or 60%.

The invention will be illustrated in the following non-limiting examples.

EXAMPLE 1

Comparative Antiglycan Antibody Levels in the Serum of Crohn's Disease Patients and Patients with other Digestive Diseases An anti-glycan antibody profile for IgG, IgA and IgM in the serum of the patients was obtained using GlycoChip® arrays (Glycominds, Ltd., Lod, Israel, Cat No. 9100). The arrays were constructed using procedures described in Schwarz et. al. Glycobiology vol. 13 no. 11 pp. 749-754, 2003. Anti-glycan antibody profiles of 45 CD patients and 27 patients with other digestive diseases were compared.

All serum samples were tested using GlycoChip® plates (Glycominds Ltd., Lod, Israel, Cat No. 9100), which was an array of mono and oligosaccharides covalently attached to a reduced volume 384 wells micro titer plate. The mono and oligosaccharides displayed on the array are listed in Table 1. A translation of the LinearCode™ syntax used to describe glycan structure to IUPAC nomenclature can be found in Table 1.

The sera from patients volunteers who had signed an informed consent form were collected by Dr. Iris Dotan for the Gastroenterology and liver disease institute in the Tel Aviv Sorasky Medical center, Israel. All patient were diagnosed by Dr. Iris Dotan. The sera were collected in evacuated silicon coated gel containing tubes (Estar Technologies Cat# 616603GLV). The sera were separated from the blood cells and kept frozen in −25° C. until use. The volume of all solutions added to the glycan array was 10 μl/well. The sera were diluted (1:20; saturating concentration) in 0.15M Tris-HCl pH 7.2, 0.085M Mg2SO4, 0.05% Tween 20 (TBST) containing 1% BSA (Sigma), dispensed into glycan array plates using a Tecan Genesis Workstation 200 automated handling system, and incubated for 60 min at 37° C. The plates were then washed with 250 μL/well Phosphate buffered Saline with 0.05% Tween 20 (PBST, Sigma) in an automatic plate washer (Tecan, POWERWASHER™). At this point the following reagents, diluted in TBST with 1% BSA, were added using a Multidrop 384 dispenser (Thermo Labsystems) and incubated for 60 min at 37° C.: for IgG, IgA, and IgM determination—the respective sub-class specific biotinylated goat anti-human Ig antibody (Jackson, Pa., USA) at 2.8 μg/ml, 3 μg/ml, and 0.9 μg/ml, respectively. Following washing with PBST, Streptavidin-conjugated europium (0.1 μg/ml) diluted in TBST with 1% BSA was added to each well followed by incubation for 30 min at 37° C. in the dark, and washing with PBST. DELFIA™ enhancement solution was then added to the wells and the plates were incubated for 30 to 45 min in the dark at room temperature. The fluorescence of the wells was read with a Victor 1420 (Wallac, Finland) plate reader using time resolved fluorescence settings of 340/612 nm (Excitation/Emission). Some patients were tested for the presence of antibodies to perinuclear anti neutrophil cytoplasmic antibodies (PANCA) and anti-*Saccharomyces cerevisiae* (ASCA) IgG and IgA using a commercial kits made by INOVA, San-Diego Calif. cat. No 708290, 708865, 708870 respectively according to the manufacturer instructions.

Tables 2 and 3 represent the levels of IgG, IgA and IgM type anti bodies anti glycan antibodies that were detected at significantly different levels between the CD population and the population with other digestive diseases. The values presented are absolute values after reduction of background. The back ground signal was measured as the signal received from wells with covalently bound p-nithrophenyl. If the result was negative the signal was scored as zero.

Comparison of the average and median values of anti-carbohydrate antibodies in the CD and other digestive disease populations reveals a significant elevation in most of the anti glycans antibodies in the CD group as compared to the group containing individuals with the other digestive diseases group. No one of the CD patients was found to be positive for pANCA antibodies. All the anti glycans levels that are displayed in Tables 2 and 3 show statistically significant ($\alpha=0.05$; $p<0.05$) different between the CD groups and the other digestive disease or normal group. Statistically significant differences between the medians of signals of CD and other digestive disease population and normal population were observed for antibodies bound to the following glycans: Glc (β), Glc (β 1-4) Glc (β), Glc (β 1-3) Glc (β), GlcNAc 6-sulfate (β), Man (α 1-2) Man (α), Man (α 1-3) Man (α), Man (α 1-6) Man (α), Man (α), Man (α 1-3)[Man (α 1-6)] Man (α), Mannan, Dextran, Xylan, GlcNAc (α 1-4) GlcNAc (β), Gal 3 sulphate (β), GlcNAc (β 1-3) GalNAc (β), GlcNAc (β 1-3) Gal (β 1-4) Glc (β), and Gal (α 1-3) Gal (β 1-4) GlcNAc (β).

Table 4 describes the specificity and sensitivity of the different IgG anti glycans for differentiation between CD and other digestive diseases using different cut-off values. The cutoff values for each glycans where set as the $89^{th}$ percentile of the non CD group.

These results reveal a set of chemically defined glycan antigens that are useful for diagnosing CD. The levels of antibodies to those glycans are higher in the CD population than in the population of normal individuals or individuals with other digestive diseases. The antibodies that showed the greatest differentiation between CD and other digestive diseases in these studies are a set of antibodies to mannose based glycan fragment as well as antibodies to Glc (β), Glc (β 1-4) Glc (β), Glc (β 1-3) Glc (β). Antibodies to Glc (β 1-3) Glc (β), Man (α 1-3) Man (α) and Man (α 1-3)[Man (α 1-6)] Man (α) were in particular able to differentiate between CD and other digestive disease at 57-62% sensitivity and 89%-93% specificity. The separation of those structures was better than what was achieved with Mannan (ASCA) 47% sensitivity and 89% specificity. Table 4 demonstrates that it is possible to use different cut-off levels and to achieve higher sensitivity but lower specificity. Table 5 describes the sensitivity, specificity, True Positives (TP), True Negative (TN), False Positives (FP), and False Negatives (FN) and positive Predictive value (PPV) in different cut-off value for differentiation between CD and other digestive disease according to the level of Anti Glc (β 1-3) Glc (β), IgG and anti Mannan IgG. FIG. 1 is a Receiver Operator Characteristic (ROC) curve for differentiation between individuals with CD and individuals with other digestive diseases according to levels of anti Glc (β 1-3) Glc (β), IgG and anti Mannan IgG antibodies.

By using combination of two or more glycans it is possible to improve the sensitivity without reducing the specificity. For example by setting cut-offs of 2000,000 for anti Glc (β 1-3) Glc (β) and 2,400,000 for anti Mannan and setting the criteria for identification of CD as individuals who are above cut-off in either of the antibodies it is possible to achieve 82% sensitivity with 70% specificity. Achieving this sensitivity by each of the antibodies alone would require to set lower cut-offs that would lead to poor specificity (37% for Glc (β 1-3) Glc (β).

EXAMPLE 2

Levels of Antiglycan Antibody Levels in the Serum of Anti-Phospholipid Syndrome (APS) Patients and Patients with other Digestive Diseases A pool of serum samples from APS patients was fractionated on a β-2 glycoprotein column and tested for the presence of anti-glycan antibodies Antibody binding was examined using GLYCOCHIP™ substrates as described in WO00/49412. Wells were blocked with ddH₂O/BSA 2.5%. The serum sample was diluted 1:2 in 1% TBST/BSA. Anti-IgA, IgG, and IgM samples were diluted 1:100 in TBST/BSA 1%. The Alexa 633 dye (Molecular Probes, Eugene, Oreg., # S-20992) was diluted 1:150 in TBST 1:150. Samples were injected using a Tescan HS4800 program. Dry arrays were scanned using an Affymetrix 428 Scanner, and images were analyzed using 'ArrayPro' software. Numerical values were exported to Excel and analyzed. For isotype determination, anti-human IgG, Fc gamma fragment specific\Biotin (Goat); Jackson; Cat # 109-065-008, anti-human IgM, Fc 5 mu fragment specific\Biotin (Goat); Jackson; Cat # 109-065-043, and anti-human serum IgA\biotin (Goat); Jackson; Cat # 109-065-011.

Figure 2A:
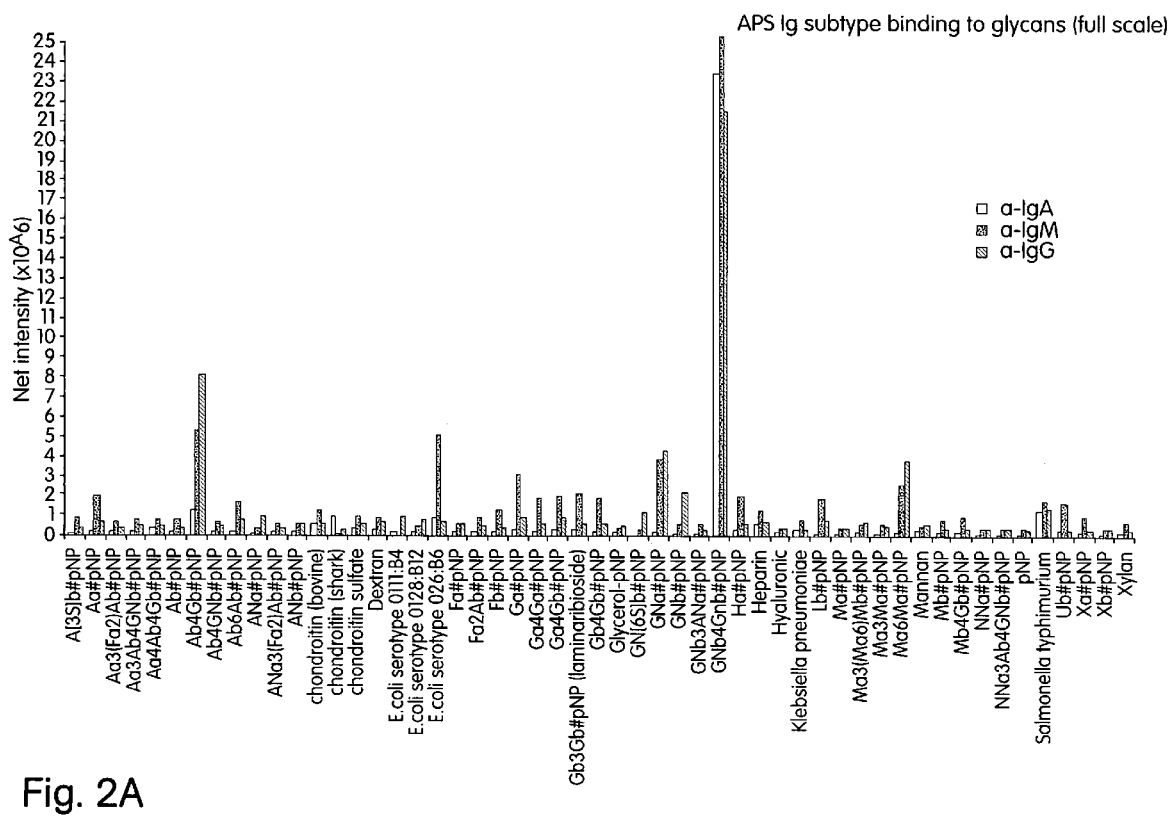
FIGS. 2A and 2B are histograms showing binding of anti-glycan antibodies to the indicated glycans in sera from patients with anti-phospholipid syndrome (APS).
Figure 2B:
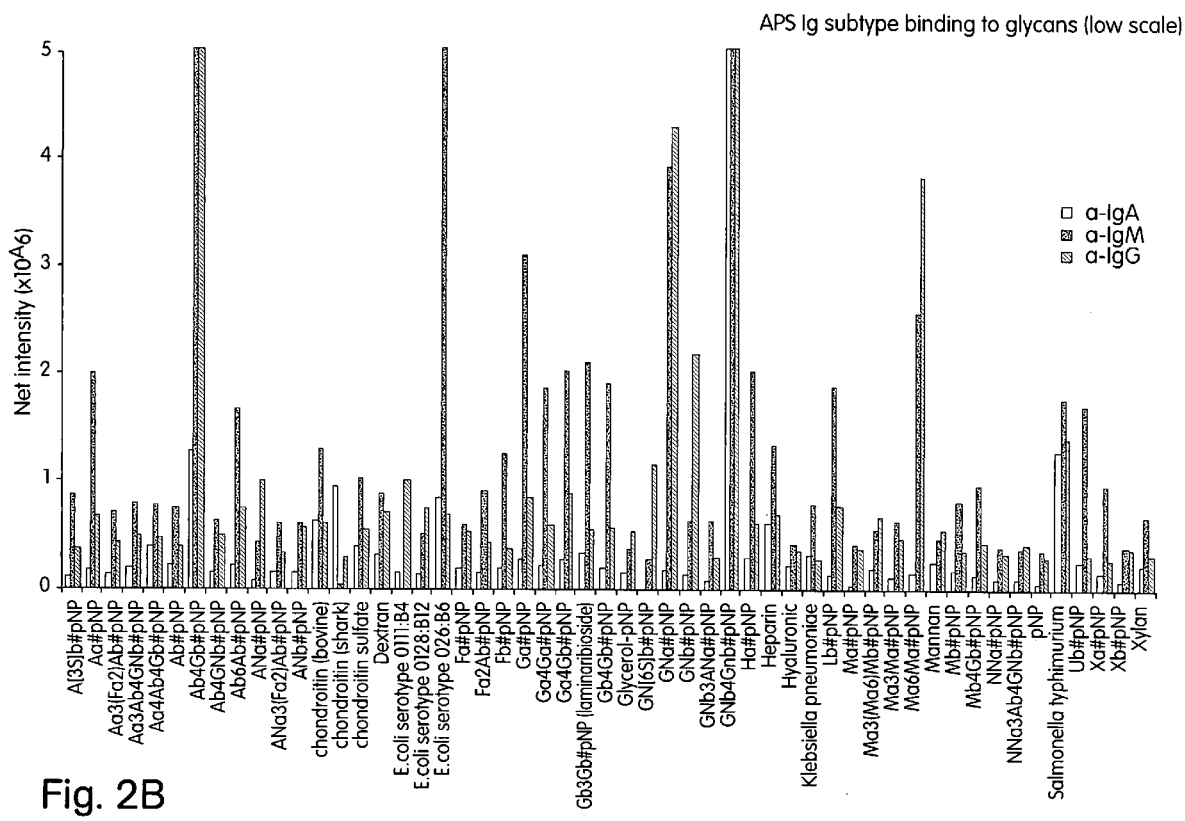

The serum sample was affinity-purified against a column of β-2-glycoprotein and then applied to a GlycoChip containing multiple glycans. The full magnitude ($0-2.5\times10^7$) of the interaction profile of the APS immunoglobulins and the tested glycans antibodies on the GlycoChip are shown in FIG. 2A. A smaller scale ($0-5\times10^6$) of the binding is shown in FIG. 2B.

The highest levels of antibodies were observed for antibodies against GlcNAc (β 1-4) GlcNAc (β) for each of the IgA, IgG, and IGM subclasses High IgG levels against LPS from

*Salmonella typhimurium*, Man (α 1-6) Man (α), GlcNAc (β), GlcNAc (β) and Gal (β 1-4) Glc (β)(Lactose) were also observed.

IgA levels were highest against GlcNAc (β 1-4) GlcNAc (β) and relatively high against Gal (β 1-4) Glc (β) and LPS from *Salmonella*. IgM levels were highest against GlcNAc (β 1-4) GlcNAc (β) and relatively high against LPS from *E. coli* O26:B6, Glucose derivatives such as Glc (α), Glc (α 1-4) Glc (β), Glc (β 1-4) Glc (β), Glc (β 1-3) Glc (β) and Glc (β 1-4) Glc (β), GlcNAc (α), Rha (α) as well as Man (α 1-6) Man (α), GalA (β), GlcA (β) and LPS from *Salmonella*. Relatively low levels of Ig were detected against the preparation of Mannan used on the GlycoChip substrate.

These results demonstrate that elevated levels antibodies to GlcNAc (β 1-4) GlcNAc (β) in the blood may serve as a marker for diagnosis of APS, and/or for the severity of the disease.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Saccharides displayed on the glycan array

| Glycan | IUPAC | LINEARCODE ® | Common Name |
|---|---|---|---|
| 0 | p-Nitrophenol | pNP-0 | |
| 1 | Gal (α) | Aa | |
| 2 | Gal (β) | Ab | |
| 3 | Gal (β1-3) GalNAc (α) | Ab3ANa | |
| 4 | Gal (β1-3) GlcNAc (β) | Ab3GNb | |
| 5 | Gal (β1-4) Glc (β) | Ab4Gb | Lactose |
| 6 | Gal (β1-6) Gal (β) | Ab6Ab | |
| 7 | GalNAc (α) | ANa | |
| 8 | GalNAc (β) | ANb | |
| 9 | Fuc (α) | Fa | |
| 10 | Fuc (β) | Fb | |
| 11 | Glc (α) | Ga | |
| 12 | Glc (α1-4) Glc (α) | Ga4Ga | Maltose |
| 13 | Glc (α1-4) Glc (β) | Ga4Gb | |
| 14 | Glc (β) | Gb | |
| 15 | Glc (β1-4) Glc (β) | Gb4Gb | Cellobiose |
| 16 | Glc (β1-4) Glc (β1-4) Glc (β) | Gb4Gb4Gb | Cellotriose |
| 17 | GlcNAc (α) | GNa | |
| 18 | GlcNAc (β) | GNb | |
| 19 | GlcNAc (β1-3) GalNAc (α) | GNb3ANa | |
| 20 | GlcNAc (β1-4) GlcNAc (β) | GNb4GNb | Chitobiose |
| 21 | L-Rha (α) | Ha | |
| 22 | GalA (β) | Lb | |
| 23 | Man (α) | Ma | |
| 24 | Man (β) | Mb | |
| 25 | Neu5Ac (α) | NNa | |
| 26 | L-Araf (α) | Ra | |
| 27 | GlcA (β) | Ub | |
| 28 | X(α) | Xa | |
| 29 | X(β) | Xb | |
| 30 | Gal (β1-3) [GlcNAc (β1-6)] GalNAc (α) | Ab3(GNb6)ANa | |
| 31 | Gal (β1-4) GlcNAc (α) | Ab4GNa | |
| 32 | Gal (α1-3) Gal (β1-4) GlcNAc (β) | Aa3Ab4GNb | Linear B-2 |
| 33 | Gal (β1-3) Gal (β1-4) GalNAc (β) | Ab4GNb | |
| 34 | Man (β1-4) GlcNAc (β) | Mb4Gb | |
| 35 | GlcNAc (β1-6)GalNAc (α) | GNb6ANa | |
| 36 | Fuc (α1-2) Gal (β) | Fa2Ab | |
| 37 | Man (α1-3) Man (α) | Ma3Ma | |
| 38 | GlcNAc (β) 6-sulfate | GN[6S]b | |
| 39 | Glc (β1-3) Glc (β) | Gb3Gb | |
| 40 | Gal(β) 3-sulfate | A[3S]b | |
| 41 | Man (α1-3) [Man (α1-6)] Man (β) | Ma3(Ma6)Mb | |
| 42 | GlcNAc (β1-3) Gal (α1-4) Glc (β) | GNb3Ab4Gb | Lacto-3 |
| 43 | Gal (α1-4) Gal (β1-4) Glc (β) | Aa4Ab4Gb | Pk antigen |
| 44 | Man (α1-6) Man α | Ma6Ma | |
| 45 | Man (α1-2) Man α | Ma2Ma | |
| 46 | Dextran | | Dextran |
| 47 | Mannam | | Mannam |
| 48 | Xylan | | Xylan |

TABLE 2

Fluorescent signals from binding of antibodies to different glycans in CD patients and non CD patients. Glycans are presented in LINEARCODE®.

| Patient No. | Clinical condition | | | | | | | | | | | |
|---|---|---|---|---|---|---|---|---|---|---|---|---|
| 10,001 | Crohn's disease | 239,525 | 979,509 | 324,062 | 28,737 | 412,186 | 145,841 | 585,222 | 4,677,868 | 0 | | |
| 10,004 | Crohn's disease | 381,122 | 3,511,076 | 2,381,922 | 0 | 0 | 0 | 1,014,289 | 2,190,867 | 956,611 | | |
| 10,005 | Crohn's disease | 7,641 | 525,203 | 13,726 | 351,139 | 0 | 0 | 0 | 3,488,820 | 0 | | |
| 10,006 | Crohn's disease | 555,734 | 62,662 | 269,512 | 78,564 | 42,543 | 0 | 48,213 | 1,091,472 | 276,481 | | |
| 10,007 | Crohn's disease | 0 | 0 | 0 | 0 | 0 | 0 | 0 | 324,492 | 0 | | |
| 10,008 | Crohn's disease | 0 | 3,186,273 | 261,521 | 0 | 0 | 0 | 2,448,511 | 1,002,289 | 0 | | |
| 10,009 | Crohn's disease | 569,715 | 454,736 | 328,022 | 167,316 | 0 | 46,886 | 2,793,801 | 874,256 | 169,975 | 80 | 33 |
| 10,011 | Crohn's disease | 435,226 | 2,467,429 | 0 | 66,968 | 0 | 0 | 3,208,701 | 918,204 | 1,180,180 | neg | |
| 10,012 | Crohn's disease | 0 | 27,402 | 214,518 | 0 | 0 | 0 | 4,269,038 | 0 | 0 | | |
| 10,013 | Crohn's disease | 91,743 | 27,235 | 51,842 | 83,080 | 0 | 0 | 372,869 | 263,911 | 3,692 | | |
| 10,015 | Crohn's disease | 1,435,731 | 1,817,947 | 2,540,714 | 303,550 | 0 | 0 | 592,410 | 2,571,728 | 30,891 | | |
| 10,016 | Crohn's disease | 906,573 | 1,994,899 | 1,971,018 | 374,644 | 84,710 | 30,478 | 6,989,275 | 2,000,621 | 416,510 | | |
| 10,018 | Crohn's disease | 521,021 | 0 | 147,106 | 0 | 0 | 0 | 7,307,560 | 0 | 434,306 | | |
| 10,021 | Crohn's disease | 554,385 | 1,317,083 | 1,000,896 | 42,976 | 0 | 0 | 609,882 | 9,322 | 285,948 | | |
| 10,025 | Crohn's disease | 885,575 | 6,891,638 | 1,217,531 | 364,637 | 188,355 | 109,598 | 3,891,841 | 1,126,417 | 0 | 49 | 54 |
| 10,026 | Crohn's disease | 539,816 | 2,154,175 | 961,447 | 327,688 | 153,606 | 123,522 | 7,130,311 | 0 | 798,295 | neg | |
| 10,027 | Crohn's disease | 113,583 | 3,559,430 | 1,182,752 | 66,965 | 0 | 257,506 | 3,708,910 | 221,962 | 511,471 | | |
| 10,028 | Crohn's disease | 0 | 1,825,768 | 169,320 | 128,581 | 84,390 | 224,520 | 4,915,018 | 1,339,734 | 84,567 | | |
| 10,031 | Crohn's disease | 20,260 | 371,507 | 159,225 | 0 | 0 | 0 | 602,554 | 0 | 0 | | |
| 10,033 | Crohn's disease | 725,599 | 344,750 | 390,943 | 340,134 | 57,574 | 328,085 | 5,299,212 | 1,173,789 | 173,028 | 108 | 34 |
| 10,034 | Crohn's disease | 227,314 | 87,267 | 850,765 | 0 | 19,046 | 34,499 | 8,102,888 | 937,019 | 0 | neg | |
| 10,036 | Crohn's disease | 391,063 | 1,425,185 | 221,359 | 185,257 | 9,877 | 35,552 | 4,729,753 | 506,773 | 270,805 | | |
| 10,041 | Crohn's disease | 2,447,847 | 7,299,442 | 1,196,749 | 554,440 | 479,128 | 279,542 | 4,912,482 | 967,370 | 1,054,697 | | |
| 10,042 | Crohn's disease | 3,075,165 | 4,137,076 | 4,847,786 | 1,141,538 | 1,382,815 | 1,065,763 | 5,218,211 | 955,444 | 0 | | |
| 10,043 | Crohn's disease | 228,780 | 5,724,798 | 5,015,655 | 0 | 657,599 | 1,131,592 | 2,611,948 | 129,079 | 3,526,456 | | |
| 10,047 | Crohn's disease | 899,158 | 5,545,432 | 762,145 | 348,988 | 11,887 | 790,941 | 4,450,715 | 0 | 281,080 | | |
| 10,058 | Crohn's disease | 1,111,889 | 3,096,078 | 998,236 | 259,305 | 284,314 | 15,398 | 3,536,621 | — | 259,435 | 9 | 18 |
| 10,060 | Crohn's disease | 3,488,594 | 5,107,549 | 3,189,052 | 861,636 | 66,108 | 365,078 | 4,557,274 | 2,812,932 | 175,351 | neg | |
| 10,061 | Crohn's disease | 302,526 | 6,708,583 | 403,578 | 63,045 | 116,816 | 886,832 | 737,419 | — | 829,159 | | |
| 10,062 | Crohn's disease | 1,970,248 | 1,880,984 | 1,712,647 | 592,484 | 479,672 | 84,505 | 5,190,198 | 4,657,297 | 26,370 | | |
| 10,064 | Crohn's disease | 923,883 | 1,722,429 | 2,323,960 | 458,720 | 1,300,332 | 287,315 | 6,597,714 | 3,696,434 | 697,255 | | |
| 10,067 | Crohn's disease | 679,589 | 2,850,072 | 1,376,044 | — | 325,777 | 2,380,047 | 1,998,817 | — | 1,478,295 | | |
| 10,068 | Crohn's disease | 412,474 | 241,622 | 307,409 | 256,696 | 501,122 | 929,191 | 29,236 | 23,386 | 800,316 | | |
| 10,071 | Crohn's disease | 1,182,752 | 3,578,889 | 708,938 | 0 | 309,375 | 1,525,473 | 3,463,114 | 2,627,120 | 711,760 | | |
| 10,073 | Crohn's disease | 547,155 | 2,551,776 | 1,018,813 | 293,958 | 1,159,788 | 289,185 | 6,630,916 | 6,178,401 | 1,576,654 | 72 | 113 |
| 10,074 | Crohn's disease | 1,849,657 | 1,705,604 | 196,196 | 150,342 | 1,020,256 | 1,611,290 | 4,060,050 | 499,170 | 608,101 | 43 | 18 |
| 10,075 | Crohn's disease | 4,173,024 | 7,209,245 | 3,339,828 | 80,395 | 1,048,834 | 1,307,139 | 6,247,571 | 5,264,056 | 2,824,132 | | |
| 10,077 | Crohn's disease | 678,576 | 1,376,957 | 658,444 | 675,875 | 420,437 | 749,060 | 228,636 | 417,861 | 302,912 | 15 | 5 |
| 10,078 | Crohn's disease | 852,494 | 2,324,221 | 2,518,629 | 740,309 | 794,975 | 209,185 | 6,306,500 | 1,744,354 | 1,191,273 | neg | 104 |
| 10,081 | Crohn's disease | 1,856,749 | 1,869,774 | 1,496,600 | 365,947 | 851,804 | 676,514 | 3,758,249 | 4,236,189 | 471,166 | 89 | 17 |
| 10,089 | Crohn's disease | 3,084,860 | 1,560,904 | 4,839,888 | 210,753 | 483,336 | 125,827 | 179,822 | 321,993 | 726,658 | 39 | 29 |
| 10,090 | Crohn's disease | 759,279 | 5,640,050 | 5,833,141 | 215,327 | 908,572 | 502,368 | 6,317,466 | 736,699 | 161,181 | 12 | |
| 10,094 | Crohn's disease | 2,153,522 | 2,067,775 | 2,215,576 | 894,280 | 1,237,060 | 250,375 | 4,098,131 | 997,472 | 954,849 | neg | |
| 10,095 | Crohn's disease | 4,905,595 | 4,327,530 | 3,460,322 | 573,036 | 797,142 | 122,830 | 6,473,836 | 302,912 | 720,792 | neg | |
| 10,102 | Crohn's disease | 445,821 | 378,722 | 797,078 | 161,173 | 245,130 | 930,156 | 115,577 | 1,187,706 | 475,933 | neg | |
| 10,051 | No digestive disease | 549,212 | 526,443 | 196,870 | 947,346 | 0 | 379,977 | 1,794,907 | 131,432 | 0 | neg | |

TABLE 2-continued

Fluorescent signals from binding of antibodies to different glycans in CD patients and non CD patients. Glycans are presented in LINEARCODE®.

| Patient No. | Clinical condition | | | | | | | | | | | | |
|---|---|---|---|---|---|---|---|---|---|---|---|---|---|
| 10,052 | No digestive disease | 560,759 | 317,476 | 367,236 | 33,889 | 5,587 | 0 | 0 | 58,482 | 356,353 | 396,032 | 0 | |
| 10,053 | No digestive disease | 57,858 | 242,565 | 0 | 50,803 | 0 | 0 | 0 | 37,486 | 503,405 | 336,286 | 25,865 | |
| 10,054 | No digestive disease | 107,351 | 78,554 | 408,109 | 95,010 | 0 | 0 | 0 | 0 | 694,824 | 1,014,501 | 0 | |
| 10,059 | Anal tissue | 349,679 | 441,239 | 0 | 0 | 117,444 | 0 | 0 | 74,490 | 2,354,312 | 228,946 | 97,181 | |
| 10,066 | Proctitis/Psoriasis | 149,491 | 174,695 | 197,496 | 95,518 | 67,661 | — | — | — | 1,088,575 | 844,179 | — | |
| 10,080 | No digestive disease | 948,557 | 1,266,954 | 885,097 | — | — | — | — | — | 1,159,558 | 1,193,312 | — | |
| 10,082 | No digestive disease | 78,069 | 1,379,223 | 710,595 | — | — | — | — | — | 4,238,190 | 1,678,410 | — | |
| 10,003 | No digestive disease | 363,362 | 312,940 | 168,366 | 347,208 | 50,843 | — | — | — | 525,545 | 361,718 | 258,224 | |
| 10,020 | Ulcerative colitis | — | 2,703,085 | — | — | — | — | — | — | 1,186,666 | 541,282 | — | |
| 10,022 | Ulcerative colitis | 340,259 | 1,732,725 | 2,209,455 | 67,238 | 0 | 0 | 0 | 0 | 4,272,493 | 2,348,955 | 0 | 40 neg |
| 10,023 | Ulcerative colitis | 90,914 | 1,209,892 | 20,926 | 0 | 267,614 | 0 | 0 | 0 | 308,161 | 93,557 | 50,612 | |
| 10,024 | Ulcerative colitis | 159,550 | 489,733 | 0 | 0 | 0 | 0 | 0 | 0 | 5,003,204 | 1,416,782 | 124,268 | |
| 10,030 | Ulcerative colitis | 1,650 | 6,963 | 58,288 | 0 | 71,007 | 0 | 0 | 0 | 1,227,240 | 606,565 | 152,946 | |
| 10,039 | Ulcerative colitis | 0 | 546,432 | 2,775,860 | 0 | 0 | 0 | 0 | 0 | 1,588,845 | 186,636 | 0 | |
| 10,040 | Ulcerative colitis | 0 | 371,648 | 33,848 | 0 | 0 | 0 | 0 | 0 | 2,838,390 | 744,886 | 1,110,942 | |
| 10,044 | Ulcerative colitis | 543,352 | 108,535 | 551,977 | 274,235 | 0 | 0 | 19,948 | 558,985 | 926,919 | 0 | | |
| 10,050 | Ulcerative colitis | 1,182,838 | 430,129 | 605,578 | 274,541 | 419,442 | 118,678 | 313,631 | 1,537,328 | 356,345 | 563,448 | | |
| 10,065 | Ulcerative colitis | 977,372 | 851,962 | 931,083 | 304,212 | 128,015 | 133,662 | 314,068 | 1,911,575 | 957,048 | 627,416 | | |
| 10,069 | Ulcerative colitis | 169,349 | 133,683 | 746,781 | 97,734 | 0 | 0 | 0 | 1,281,592 | 777,260 | 25,579 | | |
| 10,072 | Ulcerative colitis | 120,534 | 86,949 | 188,860 | 0 | 69,365 | 6,299 | 120,392 | 3,436,295 | 268,387 | 96,768 | | 8 neg 8 |
| 10,079 | Ulcerative colitis | 335,039 | 3,441,678 | 1,186,596 | 191,939 | 103,676 | 48,476 | 22,962 | — | 1,513,149 | 432,879 | 0 | |
| 10,084 | Ulcerative colitis | 446,430 | 1,574,353 | 2,292,321 | 136,761 | 184,468 | 22,962 | 21,668 | 1,096,196 | 112,154 | 101,127 | | |
| 10,086 | Ulcerative colitis | 161,202 | 379,003 | 417,320 | 36,600 | 0 | 0 | 0 | 1,699,125 | 598,760 | 47,781 | | |
| 10,087 | Ulcerative colitis | 343,325 | 156,547 | 305,446 | 114,600 | 137,647 | 57,993 | 240,234 | 1,047,544 | 110,275 | 108,383 | | 6 neg 19 |
| 10,096 | Ulcerative colitis | 413,406 | 1,461,919 | 550,499 | 94,137 | 54,108 | — | 34,517 | 4,957,039 | 186,956 | 106,274 | | |
| 10,097 | Ulcerative colitis | 125,661 | 612,367 | 622,628 | 46,173 | — | — | — | 1,426,371 | 167,573 | 10,386 | | |
| | Cutoffs in percentiles | | | | | | | | | | | | |
| | 65 | 357,204 | 582,696 | 614,956 | 96,508 | 70,268 | — | 34,771 | 1,649,499 | 682,641 | 103,958 | | |
| | 75 | 445,973 | 1,224,157 | 759,355 | 120,140 | 120,086 | 1,575 | 62,484 | 2,022,259 | 864,864 | 131,437 | | |
| | 85 | 548,919 | 1,457,784 | 928,783 | 190,400 | 182,126 | 47,200 | 118,798 | 3,406,400 | 1,011,628 | 254,645 | | |
| | 90 | 677,098 | 1,621,865 | 1,493,453 | 283,442 | 251,875 | 76,199 | 206,241 | 4,428,481 | 1,260,353 | 502,187 | | |
| | 98 | 1,071,886 | 3,042,838 | 2,514,749 | 623,271 | 341,030 | 129,870 | 313,832 | 1,978,274 | 4,066,050 | 1,986,860 | 849,837 | |
| | Average | | | | | | | | | | | | |
| | Crohn's disease | 1,036,850 | 2,487,482 | 1,419,442 | 260,564 | 354,076 | 342,420 | 465,829 | 3,823,755 | 1,489,028 | 565,479 | | |
| | No Crohn's Disease | 317,600 | 779,174 | 608,638 | 111,310 | 69,757 | 14,373 | 54,133 | 1,837,254 | 618,517 | 136,809 | | |
| | Median | | | | | | | | | | | | |
| | Crohn's disease | 596,715 | 1,880,984 | 961,447 | 185,257 | 153,606 | 91,350 | 279,542 | 4,060,050 | 937,019 | 302,912 | | |
| | No Chrohn'Disease | 169,349 | 441,239 | 408,109 | 50,803 | — | 1,426,371 | 432,879 | 47,781 | | | | |
| | nest CD vs Non CD | 0.002456446 | 0.000184349 | 0.01128244 | 0.016974961 | 0.0011162 | 0.002612017 | 0.00032205 | 0.00017892 | 0.011365107 | 0.0037420 | | |

TABLE 3

Fluorescent signals from binding of IgA and IgM antibodies to different glycans in CD patients and non CD patients. Glycans are presented in LINEARCODE ®.

| Patient No. | Clinical condition | | | | | Igm A[3S]b | IgM Aa | IgM Aa3Ab4GNb |
|---|---|---|---|---|---|---|---|---|
| 10,001 | Crohn's disease | 0 | 0 | 0 | 2,471,242 | 0 | 0 | 0 |
| 10,004 | Crohn's disease | 0 | 31,779 | 0 | 7,528,498 | 0 | 0 | 0 |
| 10,005 | Crohn's disease | 0 | 338,274 | 0 | 1,227,302 | 0 | 0 | 0 |
| 10,006 | Crohn's disease | 23,445 | 11,875 | 76,964 | 946,221 | 0 | 68,568 | 0 |
| 10,007 | Crohn's disease | 0 | 0 | 0 | 917,187 | 0 | 0 | 0 |
| 10,008 | Crohn's disease | 103,139 | 174,915 | 62,386 | 1,310,822 | 0 | 0 | 0 |
| 10,009 | Crohn's disease | 0 | 0 | 0 | 92,347 | 0 | 0 | 0 |
| 10,011 | Crohn's disease | 0 | 346,998 | 172,408 | 2,711,283 | 0 | 0 | 0 |
| 10,012 | Crohn's disease | 152,601 | 228,391 | 96,406 | 588,862 | 0 | 0 | 0 |
| 10,013 | Crohn's disease | 398,314 | 244,995 | 74,172 | 152,447 | 1,274,136 | 1,194,898 | 1,392,444 |
| 10,015 | Crohn's disease | 276,400 | 662,981 | 207,563 | 805,291 | 387,307 | 390,644 | 325,647 |
| 10,016 | Crohn's disease | 282,558 | 60,337 | 59,441 | 2,633,452 | 280,897 | 0 | 14,251 |
| 10,018 | Crohn's disease | 0 | 0 | 0 | 394,458 | 248,996 | 228,314 | 158,547 |
| 10,021 | Crohn's disease | 42,493 | 0 | 0 | 335,824 | 762,735 | 852,490 | 700,041 |
| 10,025 | Crohn's disease | 316,210 | 0 | 118,211 | 1,388,632 | 466,121 | 319,573 | 565,269 |
| 10,026 | Crohn's disease | 93,421 | 0 | 5,028 | 199,707 | 0 | 0 | 0 |
| 10,027 | Crohn's disease | 68,671 | 16,665 | 2,855 | 642,630 | 151,387 | 437,186 | 547,822 |
| 10,028 | Crohn's disease | 8,000 | 101,278 | 21,251 | 775,450 | 510,204 | 540,836 | 723,234 |
| 10,031 | Crohn's disease | 17,959 | 7,639 | 171,149 | 1,043,614 | 165,011 | 242,183 | 199,166 |
| 10,033 | Crohn's disease | 130,546 | 0 | 143,284 | 2,808,678 | 14,440 | 0 | 1,113,845 |
| 10,034 | Crohn's disease | 28,933 | 76,677 | 0 | 796,415 | 770,101 | 695,338 | 641,641 |
| 10,036 | Crohn's disease | 166,203 | 638,663 | 313,056 | 894,349 | 163,646 | 642,487 | 2,180,044 |
| 10,041 | Crohn's disease | 72,138 | 312,400 | 40,870 | 1,134,466 | 123,889 | 89,104 | 151,581 |
| 10,042 | Crohn's disease | 121,281 | 461,961 | 96,621 | 448,555 | 0 | 1,345,482 | 1,158,234 |
| 10,043 | Crohn's disease | 609,401 | 946,450 | 175,316 | 2,132,133 | 0 | 0 | 0 |
| 10,047 | Crohn's disease | 130,239 | 89,417 | 354,536 | 3,330,642 | 831,510 | 857,115 | 1,076,947 |
| 10,058 | Crohn's disease | 110,420 | 127,556 | 83,918 | 705,563 | 128,555 | 220,493 | 428,347 |
| 10,060 | Crohn's disease | 492,266 | 0 | 1,680,299 | 4,655,963 | 363,862 | 1,284,367 | 474,206 |
| 10,061 | Crohn's disease | 158,347 | 610,869 | 308,553 | 1,513,948 | 690,511 | 1,095,509 | 1,128,863 |
| 10,062 | Crohn's disease | 289,501 | 687,427 | 334,870 | 6,413,459 | 715,200 | 1,485,943 | 2,464,680 |
| 10,064 | Crohn's disease | 539,120 | 966,435 | 359,881 | 7,316,963 | 245,487 | 664,556 | 1,633,864 |
| 10,067 | Crohn's disease | 35,566 | 72,174 | 67,348 | 853,714 | 222,329 | 141,266 | 75,592 |
| 10,068 | Crohn's disease | 512,740 | 619,837 | 152,275 | 646,134 | 0 | 0 | 0 |
| 10,071 | Crohn's disease | 697,219 | 227,591 | 264,323 | 2,120,939 | 67,858 | 77,830 | 88,393 |
| 10,073 | Crohn's disease | 1,108,947 | 1,190,028 | 275,651 | 4,724,418 | 0 | 0 | 147,447 |
| 10,074 | Crohn's disease | 102,766 | 151,414 | 0 | 2,834,813 | 0 | 0 | 0 |
| 10,075 | Crohn's disease | 0 | 0 | 0 | 2,892,894 | 65,267 | 34,147 | 241,365 |
| 10,077 | Crohn's disease | 432,092 | 229,195 | 0 | 448,889 | 0 | 214,916 | 88,848 |
| 10,078 | Crohn's disease | 410,956 | 328,642 | 922,740 | 5,545,334 | 0 | 0 | 0 |
| 10,081 | Crohn's disease | 371,099 | 165,461 | 35,119 | 1,313,553 | 0 | 0 | 0 |
| 10,089 | Crohn's disease | 939,597 | 1,113,730 | 277,224 | 515,127 | 0 | 0 | 0 |
| 10,090 | Crohn's disease | 302,186 | 226,019 | 54,115 | 2,362,390 | 0 | 0 | 0 |
| 10,094 | Crohn's disease | 497,476 | 190,609 | 45,591 | 435,905 | 68,165 | 118,072 | 97,315 |
| 10,095 | Crohn's disease | 10,806 | 2,644 | 0 | 507,917 | 0 | 0 | 0 |
| 10,102 | Crohn's disease | 46,151 | 18,064 | 0 | 343,762 | 0 | 0 | 0 |
| 10,051 | No digestive disease | 47,892 | 817,025 | 0 | 563,929 | 0 | 0 | 0 |
| 10,052 | No digestive disease | 117,302 | 150,206 | 93,166 | 605,430 | 0 | 0 | 0 |
| 10,053 | No digestive disease | 38,792 | 224,900 | 0 | 215,860 | 0 | 803,031 | 314,948 |
| 10,054 | No digestive disease | 98,132 | 97,152 | 97,283 | 744,642 | 0 | 0 | 33,896 |
| 10,059 | Anal fissure | 0 | 0 | 0 | 636,387 | 0 | 0 | 0 |
| 10,066 | Proctitis/Psoriasis | 422,665 | 580,445 | 0 | 1,448,060 | 255,814 | 613,172 | 366,385 |
| 10,080 | No digestive disease | 104,079 | 137,997 | 0 | 1,279,087 | 0 | 142,813 | 1,437,670 |
| 10,082 | No digestive disease | 1,071,426 | 53,617 | 17,586 | 833,228 | 0 | 0 | 0 |
| 10,003 | Ulcerative colitis | 8,237 | 26,105 | 0 | 823,317 | 0 | 0 | 0 |
| 10,020 | Ulcerative colitis | 0 | 0 | 0 | 524,406 | 0 | 0 | 0 |
| 10,022 | Ulcerative colitis | 0 | 0 | 0 | 739,593 | 0 | 0 | 230,936 |
| 10,023 | Ulcerative colitis | 259,476 | 0 | 0 | 685,296 | 0 | 0 | 0 |
| 10,024 | Ulcerative colitis | 0 | 0 | 24,598 | 639,507 | 0 | 0 | 0 |
| 10,030 | Ulcerative colitis | 0 | 0 | 76,523 | 1,016,276 | 0 | 0 | 0 |
| 10,039 | Ulcerative colitis | 48,020 | 11,750 | 0 | 846,823 | 0 | 0 | 0 |
| 10,040 | Ulcerative colitis | 0 | 0 | 0 | 831,587 | 0 | 0 | 0 |
| 10,044 | Ulcerative colitis | 11,952 | 83,214 | 18,860 | 413,193 | 7,575 | 99,214 | 210,443 |
| 10,050 | Ulcerative colitis | 51,955 | 5,070 | 0 | 360,267 | 0 | 0 | 0 |
| 10,065 | Ulcerative colitis | 0 | 101,517 | 0 | 464,560 | 646,009 | 651,393 | 679,823 |
| 10,069 | Ulcerative colitis | 9,590 | 0 | 38,568 | 419,600 | 0 | 0 | 0 |
| 10,072 | Ulcerative colitis | 7,293 | 0 | 15,179 | 999,491 | 0 | 0 | 0 |
| 10,079 | Ulcerative colitis | 0 | 0 | 35,661 | 603,017 | 0 | 79,891 | 36,805 |
| 10,084 | Ulcerative colitis | 0 | 0 | 0 | 428,114 | 0 | 0 | 0 |
| 10,086 | Ulcerative colitis | 0 | 0 | 0 | 607,351 | 16,235 | 221,934 | 0 |
| 10,087 | Ulcerative colitis | 262,818 | 0 | 12,060 | 873,344 | 175,021 | 175,678 | 321,514 |
| 10,096 | Ulcerative colitis | — | — | 56,446 | 371,917 | — | — | — |
| 10,097 | Ulcerative colitis | — | — | 40,759 | 571,976 | — | — | — |
| | Average | | | | | | | |
| | Crohn's disease | 224,427 | 259,542 | 156,743 | 1,797,182 | 193,725 | 294,251 | 395,947 |

TABLE 3-continued

Fluorescent signals from binding of IgA and IgM antibodies to different glycans in CD patients and non CD patients. Glycans are presented in LINEARCODE ®.

|  |  |  |  |  |  |  |  |
|---|---|---|---|---|---|---|---|
| No Chrohn'Disease Median | 94,838 | 84,778 | 19,507 | 686,898 | 40,765 | 103,227 | 134,534 |
| Crohn's disease | 121,281 | 151,414 | 67,348 | 1,043,614 | 14,440 | 68,568 | 88,848 |
| No Chrohn's Disease | 8,237 | — | — | 636,387 | — | — | — |
| ttest CD vs Non CD | 0.034732158 | 0.013016159 | 0.0156334 | 0.002570494 | 0.014433781 | 0.036400897 | 0.041051138 |

| Patient No. | Clinical condition | IgM Aa4Ab4Gb | IgM Ab3(GNb6)ANa | IgM Ab3ANa | IgM GNb3Ab4Gb | IgM GNb3ANa | IgM Dextran | IgM Mannan |
|---|---|---|---|---|---|---|---|---|
| 10,001 | Crohn's disease | 0 | 0 | 0 | 608,457 | 657,592 | 230,160 | 2,084,216 |
| 10,004 | Crohn's disease | 0 | 0 | 0 | 542,436 | 730,879 | 360,390 | 722,969 |
| 10,005 | Crohn's disease | 0 | 161,405 | 0 | 1,375,070 | 2,933,445 | 388,048 | 117,931 |
| 10,006 | Crohn's disease | 402,561 | 166,017 | 0 | 1,695,894 | 1,963,416 | 3,110,617 | 810,5025 |
| 10,007 | Crohn's disease | 0 | 0 | 0 | 1,178,646 | 993,402 | 969,884 | 612,220 |
| 10,008 | Crohn's disease | 0 | 0 | 0 | 735,201 | 1,372,932 | 468,089 | 796,727 |
| 10,009 | Crohn's disease | 0 | 0 | 0 | 322,451 | 680,970 | 59,317 | 0 |
| 10,011 | Crohn's disease | 0 | 0 | 0 | 205,150 | 1,039,057 | 494,848 | 0 |
| 10,012 | Crohn's disease | 0 | 0 | 0 | 972,528 | 1,688,071 | 1,221,314 | 1,490,590 |
| 10,013 | Crohn's disease | 0 | 0 | 0 | 1,174,565 | 2,419,276 | 2,049,830 | 2,588,785 |
| 10,015 | Crohn's disease | 0 | 0 | 0 | 1,054,492 | 1,545,327 | 2,107,182 | 1,418,006 |
| 10,016 | Crohn's disease | 0 | 0 | 0 | 1,328,058 | 3,127,245 | 1,667,531 | 70,238 |
| 10,018 | Crohn's disease | 0 | 0 | 0 | 1,430,548 | 1,912,812 | 2,166,938 | 1,971,045 |
| 10,021 | Crohn's disease | 0 | 327,738 | 4,353 | 1,469,658 | 2,142,999 | 2,094,545 | 1,285,376 |
| 10,025 | Crohn's disease | 0 | 0 | 0 | 2,975,994 | 3,777,466 | 2,312,303 | 2,435,341 |
| 10,026 | Crohn's disease | 0 | 0 | 0 | 745,061 | 3,384,432 | 3,509,606 | 409,591 |
| 10,027 | Crohn's disease | 0 | 0 | 0 | 1,779,829 | 3,425,917 | 1,720,479 | 3,144,625 |
| 10,028 | Crohn's disease | 0 | 81,777 | 46,618 | 1,562,488 | 2,857,289 | 2,236,531 | 3,049,138 |
| 10,031 | Crohn's disease | 0 | 15,958 | 0 | 578,140 | 849,394 | 973,540 | 910,393 |
| 10,033 | Crohn's disease | 0 | 0 | 0 | 879,981 | 1,786,910 | 822,422 | 587,545 |
| 10,034 | Crohn's disease | 0 | 121,757 | 78,717 | 1,117,458 | 1,646,989 | 1,616,572 | 1,320,077 |
| 10,036 | Crohn's disease | 0 | 0 | 0 | 2,573,605 | 2,518,175 | 2,570,459 | 1,552,108 |
| 10,041 | Crohn's disease | 0 | 0 | 0 | 781,745 | 1,733,620 | 929,763 | 1,789,860 |
| 10,042 | Crohn's disease | 0 | 0 | 0 | 2,298,533 | 3,652,328 | 4,851,471 | 1,342,805 |
| 10,043 | Crohn's disease | 0 | 0 | 0 | 943,254 | 3,801,228 | 349,534 | 628,039 |
| 10,047 | Crohn's disease | 0 | 465,551 | 147,112 | 1,854,934 | 3,495,774 | 3,233,236 | 1,936,982 |
| 10,058 | Crohn's disease | 0 | 0 | 0 | 897,206 | 1,775,488 | 766,028 | 983,376 |
| 10,060 | Crohn's disease | 0 | 19,714 | 0 | 926,098 | 2,910,549 | 1,296,914 | 859,571 |
| 10,061 | Crohn's disease | 0 | 621,675 | 149,877 | 2,612,378 | 3,589,958 | 2,379,098 | 4,685,631 |
| 10,062 | Crohn's disease | 0 | 220,921 | 188,832 | 1,464,405 | 2,716,333 | 1,256,919 | 1,245,680 |
| 10,064 | Crohn's disease | 0 | 635,144 | 0 | 1,893,522 | 3,343,233 | 2,212,175 | 2,923,034 |
| 10,067 | Crohn's disease | 0 | 0 | 0 | 631,443 | 1,765,852 | 1,280,499 | 1,011,954 |
| 10,068 | Crohn's disease | 0 | 0 | 0 | 0 | 829,715 | 0 | 0 |
| 10,071 | Crohn's disease | 0 | 272,031 | 0 | 669,203 | 1,023,200 | 302,307 | 2,573,082 |
| 10,073 | Crohn's disease | 30,339 | 184,079 | 5,781 | 693,896 | 1,180,873 | 1,506,812 | 2,148,575 |
| 10,074 | Crohn's disease | 0 | 0 | 0 | 1,549,121 | 2,082,886 | 1,385,468 | 531,246 |
| 10,075 | Crohn's disease | 0 | 65,722 | 0 | 839,403 | 1,814,627 | 1,571,440 | 582,384 |
| 10,077 | Crohn's disease | 0 | 321,513 | 0 | 576,897 | 1,309,189 | 1,059,111 | 359,244 |
| 10,078 | Crohn's disease | 0 | 0 | 0 | 43,955 | 952,620 | 464,210 | 791,441 |
| 10,081 | Crohn's disease | 0 | 0 | 0 | 28,386 | 907,289 | 0 | 93,410 |
| 10,089 | Crohn's disease | 0 | 0 | 0 | 0 | 319,608 | 309,448 | 0 |
| 10,090 | Crohn's disease | 0 | 6,781 | 0 | 326,922 | 551,737 | 253,387 | 635,071 |
| 10,094 | Crohn's disease | 93,394 | 70,477 | 4,567 | 427,222 | 634,599 | 741,918 | 1,331,605 |
| 10,095 | Crohn's disease | 0 | 0 | 0 | 331,811 | 1,357,109 | 711,417 | 2,803,494 |
| 10,102 | Crohn's disease | 0 | 0 | 0 | 0 | 78,782 | 0 | 860,022 |
| 10,051 | No digestive disease | 0 | 0 | 0 | 0 | 0 | 70,898 | 0 |
| 10,052 | No digestive disease | 0 | 0 | 0 | 0 | 0 | 0 | 0 |
| 10,053 | No digestive disease | 0 | 0 | 0 | 909,819 | 1,957,899 | 2,693,514 | 160,549 |
| 10,054 | No digestive disease | 86,151 | 118,374 | 0 | 1,417,516 | 2,034,746 | 1,190,821 | 0 |
| 10,059 | Anal fissure | 47,680 | 0 | 0 | 621,074 | 860,869 | 553,501 | 0 |
| 10,066 | Proctitis/Psoriasis | 711,585 | 672,896 | 648,481 | 1,399,015 | 2,112,942 | 2,036,326 | 2,851,646 |
| 10,080 | No digestive disease | 357,136 | 255,635 | 13,016 | 682,951 | 1,753,399 | 466,998 | 226,598 |
| 10,082 | No digestive disease | 361,634 | 265,794 | 58,052 | 1,059,304 | 3,803,965 | 460,919 | 0 |
| 10,003 | Ulcerative colitis | 0 | 0 | 0 | 0 | 0 | 0 | 0 |
| 10,020 | Ulcerative colitis | 0 | 0 | 0 | 0 | 0 | 0 | 0 |
| 10,022 | Ulcerative colitis | 5,354 | 0 | 0 | 530,365 | 1,220,301 | 910,810 | 0 |
| 10,023 | Ulcerative colitis | 538,071 | 0 | 0 | 345,812 | 630,728 | 401,625 | 109,462 |
| 10,024 | Ulcerative colitis | 119,591 | 2,544,871 | 64,642 | 1,271,762 | 2,775,365 | 877,756 | 1,161,681 |
| 10,030 | Ulcerative colitis | 0 | 79,886 | 60,684 | 606,210 | 622,605 | 1,558,797 | 0 |
| 10,039 | Ulcerative colitis | 0 | 26,754 | 32,355 | 732,277 | 910,699 | 542,797 | 51,325 |
| 10,040 | Ulcerative colitis | 0 | 0 | 0 | 798,350 | 1,289,960 | 751,879 | 156,868 |
| 10,044 | Ulcerative colitis | 53,421 | 548,458 | 59,039 | 402,433 | 873,504 | 961,761 | 697,203 |
| 10,050 | Ulcerative colitis | 0 | 0 | 0 | 445,848 | 728,257 | 737,999 | 134,037 |
| 10,065 | Ulcerative colitis | 669,033 | 381,610 | 201,783 | 1,203,436 | 1,975,174 | 1,363,891 | 1,024,417 |
| 10,069 | Ulcerative colitis | 0 | 0 | 0 | 1,127,666 | 1,331,796 | 0 | 313,657 |
| 10,072 | Ulcerative colitis | 0 | 375,381 | 0 | 825,856 | 1,084,765 | 2,081,853 | 556,681 |
| 10,079 | Ulcerative colitis | 512,305 | 182,972 | 79,189 | 828,413 | 1,477,648 | 992,691 | 696,436 |

TABLE 3-continued

Fluorescent signals from binding of IgA and IgM antibodies to different glycans in CD patients and non CD patients. Glycans are presented in LINEARCODE ®.

| | | | | | | | | |
|---|---|---|---|---|---|---|---|---|
| 10,084 | Ulcerative colitis | 0 | 0 | 0 | 650,663 | 1,075,158 | 309,983 | 489,824 |
| 10,086 | Ulcerative colitis | 293,278 | 0 | 0 | 835,147 | 1,931,046 | 1,405,512 | 824,630 |
| 10,087 | Ulcerative colitis | 145,748 | 337,665 | 220,927 | 592,753 | 1,540,709 | 897,343 | 1,016,898 |
| 10,096 | Ulcerative colitis | — | — | — | 331,000 | 441,228 | 452,374 | 582,057 |
| 10,097 | Ulcerative colitis | — | 1,022,582 | 33,778 | 854,116 | 2,517,741 | 913,480 | 517,995 |
| | Average | | | | | | | |
| | Crohn's disease | 11,695 | 83,517 | 13,908 | 1,024,356 | 1,895,124 | 1,333,594 | 1,277,643 |
| | No Chrohn'Disease | 144,481 | 252,329 | 54,516 | 684,140 | 1,294,463 | 838,279 | 429,258 |
| | Median | | | | | | | |
| | Crohn's disease | — | — | — | 897,206 | 1,765,852 | 1,221,314 | 983,376 |
| | No Chrohn's Disease | — | — | — | 682,951 | 1,220,301 | 751,879 | 160,549 |
| | ttest CD vs Non CD | 0.000390828 | 0.047775166 | 0.059924749 | 0.029702213 | 0.017590683 | 0.034573847 | 0.000253081 |

TABLE 4

Specificity and sensitivity of the different IgG anti glycans for differentiation between CD and other digestive diseases using different cut-off values. The cutoff values for each glycans were set as the 89th percentiles of the other digestive disease group. Glycans are presented in linear code.

| | | Anti Glycan IgG antibodies | | | | | | | | | |
|---|---|---|---|---|---|---|---|---|---|---|---|
| Cut-off level | | Gb | Gb3Gb | Gb4Gb | GN[6S]b | Ma | Ma3(Ma6)Mb | Ma3Ma | Mannan | Xylan | Ma2Ma |
| 65 percentile of non CD | Sensitivity for CD % | 76 | 73 | 62 | 62 | 58 | 60 | 71 | 78 | 58 | 71 |
| | Specificity for CD % | 70 | 63 | 67 | 70 | 67 | 78 | 70 | 67 | 63 | 67 |
| 75 percentile of non CD | Sensitivity for CD % | 62 | 71 | 58 | 60 | 71 | 60 | 64 | 73 | 62 | 71 |
| | Specificity for CD % | 74 | 74 | 78 | 78 | 52 | 78 | 78 | 74 | 74 | 78 |
| 85 percentile of non CD | Sensitivity for CD % | 56 | 64 | 51 | 49 | 49 | 56 | 62 | 67 | 40 | 62 |
| | Specificity for CD % | 81 | 81 | 81 | 81 | 85 | 85 | 81 | 81 | 81 | 85 |
| 90 percentile of non CD | Sensitivity for CD % | 49 | 62 | 33 | 42 | 44 | 56 | 60 | 47 | 36 | 40 |
| | Specificity for CD % | 89 | 89 | 89 | 89 | 89 | 93 | 89 | 89 | 89 | 89 |

TABLE 5

The sensitivity, specificity, True Positives (TP), True Negative (TN), False Positives (FP), and False Negatives (FN), and Positive Predictive Value (PPV) in different cut-of values for differentiation between CD and other digestive disease according to the level of Anti-Glc ($\beta$ 1–3) Glc ($\beta$) IgG.

| | IgG Gb3Gb (abnormals above cut-off) | Sensitivity | Specificity | TP | TN | FP | FN | PPV |
|---|---|---|---|---|---|---|---|---|
| TRA 1858358v1 | — | 100.0% | 0.0% | 45 | 0 | 27 | 0 | 62.5 |
| | 0 | 95.6% | 0.0% | 43 | 0 | 27 | 2 | 61.43 |
| | 6,963 | 95.6% | 3.7% | 43 | 1 | 26 | 2 | 62.32 |
| | 27,235 | 93.3% | 3.7% | 42 | 1 | 26 | 3 | 61.76 |
| | 27,402 | 91.1% | 3.7% | 41 | 1 | 26 | 4 | 61.19 |
| | 62,662 | 88.9% | 3.7% | 40 | 1 | 26 | 5 | 60.61 |
| | 78,554 | 88.9% | 7.4% | 40 | 2 | 25 | 5 | 61.54 |
| | 86,949 | 88.9% | 11.1% | 40 | 3 | 24 | 5 | 62.5 |
| | 87,267 | 86.7% | 11.1% | 39 | 3 | 24 | 6 | 61.9 |
| | 108,535 | 86.7% | 14.8% | 39 | 4 | 23 | 6 | 62.9 |
| | 133,683 | 86.7% | 18.5% | 39 | 5 | 22 | 6 | 63.93 |
| | 156,547 | 86.7% | 22.2% | 39 | 6 | 21 | 6 | 65 |
| | 174,695 | 86.7% | 25.9% | 39 | 7 | 20 | 6 | 68.1 |
| | 241,622 | 84.4% | 25.9% | 38 | 7 | 20 | 7 | 65.52 |
| | 242,565 | 84.4% | 29.6% | 38 | 8 | 19 | 7 | 66.67 |
| | 312,940 | 84.4% | 33.3% | 38 | 9 | 18 | 7 | 67.86 |
| | 317,476 | 84.4% | 37.0% | 38 | 10 | 17 | 7 | 69.09 |
| | 344,750 | 82.2% | 37.0% | 37 | 10 | 17 | 8 | 68.52 |
| | 371,507 | 80.0% | 37.0% | 36 | 10 | 16 | 9 | 67.92 |
| | 371,648 | 80.0% | 40.7% | 36 | 11 | 16 | 9 | 69.23 |
| | 378,722 | 77.8% | 40.7% | 35 | 11 | 15 | 10 | 68.63 |
| | 379,003 | 77.8% | 44.4% | 35 | 12 | 14 | 10 | 70 |
| | 430,129 | 77.8% | 48.1% | 35 | 13 | 13 | 10 | 71.43 |
| | 441,239 | 77.8% | 51.9% | 35 | 14 | 13 | 10 | 72.92 |

TABLE 5-continued

The sensitivity, specificity, True Positives (TP), True Negative (TN), False Positives (FP), and False Negatives (FN), and Positive Predictive Value (PPV) in different cut-of values for differentiation between CD and other digestive disease according to the level of Anti-Glc (β 1–3) Glc (β) IgG.

| IgG Gb3Gb (abnormals above cut-off) | Sensitivity | Specificity | TP | TN | FP | FN | PPV |
|---|---|---|---|---|---|---|---|
| 454,736 | 75.6% | 51.9% | 34 | 14 | 13 | 11 | 72.34 |
| 489,733 | 75.6% | 55.6% | 34 | 15 | 12 | 11 | 73.91 |
| 525,203 | 73.3% | 55.6% | 33 | 15 | 12 | 12 | 73.33 |
| 526,443 | 73.3% | 59.3% | 33 | 16 | 11 | 12 | 75 |
| 546,432 | 73.3% | 63.0% | 33 | 17 | 10 | 12 | 76.74 |
| 612,367 | 73.3% | 66.7% | 33 | 18 | 9 | 12 | 78.57 |
| 851,962 | 73.3% | 70.4% | 33 | 19 | 8 | 12 | 80.49 |
| 979,509 | 71.1% | 70.4% | 32 | 19 | 8 | 13 | 80 |
| 1,209,892 | 71.1% | 74.1% | 32 | 20 | 7 | 13 | 82.05 |
| 1,266,954 | 71.1% | 77.8% | 32 | 21 | 6 | 13 | 84.21 |
| 1,317,083 | 68.9% | 77.8% | 31 | 21 | 6 | 14 | 83.78 |
| 1,376,957 | 66.7% | 77.8% | 30 | 21 | 6 | 15 | 83.33 |
| 1,379,223 | 66.7% | 81.5% | 30 | 22 | 5 | 15 | 85.71 |
| 1,425,185 | 64.4% | 81.5% | 29 | 22 | 5 | 16 | 85.29 |
| 1,461,919 | 64.4% | 85.2% | 29 | 23 | 4 | 16 | 87.88 |
| 1,560,904 | 62.2% | 85.2% | 28 | 23 | 4 | 17 | 87.5 |
| 1,574,353 | 62.2% | 88.9% | 28 | 24 | 3 | 17 | 90.32 |
| 1,705,604 | 60.0% | 88.9% | 27 | 24 | 3 | 18 | 90 |
| 1,722,429 | 57.8% | 88.9% | 26 | 24 | 3 | 19 | 89.66 |
| 1,732,725 | 57.8% | 92.6% | 26 | 25 | 2 | 19 | 92.86 |
| 1,817,947 | 55.6% | 92.6% | 25 | 25 | 2 | 20 | 92.59 |
| 1,825,768 | 53.3% | 92.6% | 24 | 25 | 2 | 21 | 92.31 |
| 1,869,774 | 51.1% | 92.6% | 23 | 25 | 2 | 22 | 92 |
| 1,880,984 | 48.9% | 92.6% | 22 | 25 | 2 | 23 | 91.67 |
| 1,994,899 | 46.7% | 92.6% | 21 | 25 | 2 | 24 | 91.3 |
| 2,067,775 | 44.4% | 92.6% | 20 | 25 | 2 | 25 | 90.91 |
| 2,154,175 | 42.2% | 92.6% | 19 | 25 | 2 | 26 | 90.48 |
| 2,324,221 | 40.0% | 92.6% | 18 | 25 | 2 | 27 | 90 |
| 2,467,429 | 37.8% | 92.6% | 17 | 25 | 2 | 28 | 89.47 |
| 2,551,776 | 35.6% | 92.6% | 16 | 25 | 2 | 29 | 88.89 |
| 2,703,085 | 35.6% | 96.3% | 16 | 26 | 1 | 29 | 94.12 |
| 2,850,072 | 33.3% | 96.3% | 15 | 26 | 1 | 30 | 93.75 |
| 3,096,078 | 31.1% | 96.3% | 14 | 26 | 1 | 31 | 93.33 |
| 3,186,273 | 28.9% | 96.3% | 13 | 26 | 1 | 32 | 92.86 |
| 3,441,678 | 28.9% | 100.0% | 13 | 27 | 0 | 32 | 100 |
| 3,511,076 | 26.7% | 100.0% | 12 | 27 | 0 | 33 | 100 |
| 3,559,430 | 24.4% | 100.0% | 11 | 27 | 0 | 34 | 100 |
| 3,578,889 | 22.2% | 100.0% | 10 | 27 | 0 | 35 | 100 |
| 4,137,076 | 20.0% | 100.0% | 9 | 27 | 0 | 36 | 100 |
| 4,327,530 | 17.8% | 100.0% | 8 | 27 | 0 | 37 | 100 |
| 5,107,549 | 15.6% | 100.0% | 7 | 27 | 0 | 38 | 100 |
| 5,545,432 | 13.3% | 100.0% | 6 | 27 | 0 | 39 | 100 |
| 5,640,050 | 11.1% | 100.0% | 5 | 27 | 0 | 40 | 100 |
| 5,724,798 | 8.9% | 100.0% | 4 | 27 | 0 | 41 | 100 |
| 6,708,583 | 6.7% | 100.0% | 3 | 27 | 0 | 42 | 100 |
| 6,891,638 | 4.4% | 100.0% | 2 | 27 | 0 | 43 | 190 |
| 7,209,245 | 2.2% | 100.0% | 1 | 27 | 0 | 44 | 100 |
| 7,299,442 | 0.0% | 100.0% | 0 | 27 | 0 | 45 | ##### |

What is claimed is:

1. A method of diagnosing Crohn's disease in a subject, the method comprising
    providing a test sample from a subject with digestive symptoms of Crohn's disease;
    detecting a level of an IgA anti-GlcNAc (β 1-4) GlcNAc (β) antibody (ACCA) in said sample by binding of said IgA ACCA in said sample to a carbohydrate reagent comprising an isolated GlcNAc (β 1-4) GlcNAc (β) glycan; and
    diagnosing Crohn's Disease in said subject by detection of an elevated level of said IgA ACCA in said test sample relative to a control reference level.

2. The method of claim 1, wherein said control reference level is a level from one or more individuals without Crohn's disease.

3. The method of claim 1, wherein said control reference level is a level from one or more individuals with a gastrointestinal disorder that is irritable bowel syndrome or ulcerative colitis.

4. The method of claim 1, wherein said control reference level is a level from one or more individuals that do not have a gastrointestinal disorder.

5. The method of claim 1, wherein said ACCA is detected with a fluorescent antibody.

6. The method of claim 1, wherein said ACCA is detected with an enzyme-linked immunoabsorbent assay (ELISA).

7. The method of claim 1, wherein said method further comprises detecting a level of an anti-Glc (β 1-3) Glc (β) antibody (ALCA) or an anti-polysaccharide β-D (1-3) Glucan antibody in said sample, wherein said subject is assessed as having Crohn's disease if said ALCA or said polysaccharide β-D (1-3) Glucan antibody levels are elevated in said sample relative to a control reference level.

8. The method of claim 7, further comprising determining an isotype of said anti-Glc (β 1-3) Glc (β) antibody or said anti-polysaccharide β-D (1-3) Glucan antibody in said sample.

9. The method of claim 8, wherein said anti-Glc (β 1-3) Glc (β) antibody or said anti-polysaccharide β-D (1-3) Glucan antibody in said sample is an IgA isotype antibody.

10. The method of claim 8, wherein said anti-Glc (β 1-3) Glc (β) antibody or said anti-polysaccharide β-D (1-3) Glucan antibody in said sample is an IgC isotype antibody.

11. The method of claim 10, wherein said method further comprises detecting a level of an anti-Glc (β) IgG antibody, an anti-Glc (β 1-3) Glc (β) IgG antibody, an anti-Glc (β 1-4) Glc (β) IgG antibody, an anti-GlcNAc (β) 6-sulfate IgG antibody, or an anti-Xylan IgG antibody in said sample, wherein said subject is assessed as having Crohn's disease if the levels of each of said detected antibodies are elevated in said sample relative to a control reference level.

12. The method of claim 1, wherein said method further comprises detecting a level of an anti-Glc (β 1-3) Glc (β) antibody (ALCA) and an anti-polysaccharide β-D (1-3) Glucan antibody in said sample, wherein said subject is assessed as having Crohn's disease if said ALCA and said polysaccharide (β 1-3) Glucan antibody levels are elevated in said sample relative to a control reference level.

13. The method of claim 1, further comprising
detecting a level of an anti-Glc (β 1-3) Glc (β) antibody (ALCA) in said sample by binding of said ALCA in said sample to a carbohydrate reagent comprising an isolated Glc (β 1-3) Glc (β) glycan and
diagnosing Crohn's Disease in said subject by detection of an elevated level of said anti-Glc (β 1-3) Glc (β) antibody in said test sample relative to a control reference level.

14. The method of claim 1, further comprising determining whether said test sample has anti-neutrophil cytoplasmic antibodies (ANCA), wherein the subject is assessed as having Crohn's Disease if said ANCA are absent from said sample.

15. The method of claim 1, further comprising detecting in said test sample a level of an anti-Mannan antibody (ASCA), wherein the subject is assessed as having Crohn's disease if said ASCA levels are elevated in said sample relative to a control reference level.

16. The method of claim 15, further comprising determining whether said test sample has anti-neutrophil cytoplasmic antibodies (ANCA), wherein the subject is assessed as having Crohn's Disease if said ANCA are absent from said sample.

17. The method of claim 1, further comprising
detecting a level of an anti-mannan antibody (ASCA) in said sample by binding of said ASCA in said sample to a carbohydrate reagent comprising an isolated mannan and
diagnosing Crohn's Disease in said subject by detection of an elevated level of said anti-mannan antibody in said test sample relative to a control reference level.

18. The method of claim 1, wherein said method further comprises detecting a level of one, two, or three of anti-Man (α 1-3)[Man (α 1-6)] Man (α) antibody, anti-Man (α 1-2) Man (α) antibody, anti-Man (α 1-6) Man (α) antibody (AMCA) or an anti-Mannan antibody (ASCA) in said sample, wherein said subject is assessed as having Crohn's disease if the levels of each of said detected antibodies are elevated in said sample relative to a control reference level.

19. The method of claim 1, further comprising
detecting a level of an anti-Man (α 1-3) Man (α) antibody (AMCA) in said sample by binding of said AMCA in said sample to a carbohydrate reagent comprising an isolated Man (α 1-3) Man (α) glycan and
diagnosing Crohn's Disease in said subject by detection of an elevated level of said anti-Man (α 1-3) Man (α) antibody in said test sample relative to a control reference level.

20. The method of claim 1, wherein said test sample is a biological fluid.

21. The method of claim 20, wherein said biological fluid is whole blood, serum, plasma, urine, or saliva.

22. The method of claim 20, wherein said biological fluid is serum.

23. A method of diagnosing Crohn's disease in a subject, the method comprising
providing a test sample from a subject with digestive symptoms of Crohn's disease;
detecting a level of an anti-Glc (β 1-3) Glc (β) antibody (ALCA) in said sample by binding of said ALCA in said sample to a carbohydrate reagent comprising an isolated Glc (β 1-3) Glc (β) glycan; and
diagnosing Crohn's Disease in said subject by detection of an elevated level of said antibody in said test sample relative to a control reference level.

24. The method of claim 23, wherein said method comprises detecting a level of an IgG ALCA in said sample.

25. The method of claim 24, wherein said method further comprises detecting a level of an IgG anti-Man (α 1-3) Man (α) antibody in said sample, wherein said subject is assessed as having Crohn's disease if said IgG anti-Man (α 1-3) Man (α) antibody level is elevated in said sample relative to a control reference level.

26. The method of claim 23, wherein said method comprises detecting a level of an IgG anti-Glc (β 1-3) Glc (β) antibody (ALCA) and an IgG anti-Man (α 1-3) Man (α) antibody (AMCA) in said sample, wherein said subject is assessed as having Crohn's disease if said IgG ALCA and said IgG AMCA levels are elevated in said sample relative to a control reference level.

27. The method of claim 23, wherein said method further comprises detecting a level of an IgG anti-Mannan antibody (ASCA) or an IgA anti-Mannan antibody (ASCA) in said sample, wherein said subject is assessed as having Crohn's Disease if said IgG ASCA or said IgA ASCA is elevated in said sample relative to a control reference level.

28. The method of claim 27, wherein said method comprises detecting the level of IgG ASCA in said sample.

29. The method of claim 27, wherein said method comprises detecting the level of IgA ASCA in said sample.

30. The method of claim 27, wherein said method further comprises determining whether said sample has anti-neutrophil cytoplasmic antibodies (ANCA), wherein said subject is assessed as having Crohn's Disease if said ANCA are absent from said sample.

31. The method of claim 23, wherein said control reference level is a level from one or more individuals without Crohn's disease.

32. The method of claim 23, wherein said control reference level is a level from one or more individuals with a gastrointestinal disorder that is irritable bowel syndrome or ulcerative colitis.

33. The method of claim 23, wherein said control reference level is a level from one or more individuals that do not have a gastrointestinal disorder.

34. The method of claim 23, wherein said ALCA is detected with a fluorescent antibody.

35. The method of claim 23, wherein said ALCA is detected with an enzyme-linked inununoabsorbent assay (ELISA).

36. The method of claim 23, further comprising determining an isotype of said antibody, wherein said antibody is an IgA isotype antibody.

37. The method of claim 23, wherein said method further comprises detecting a level of an anti-GlcNAc (β 1-4) GleNAc (β) antibody (ACCA) or an anti-polysaceharide β-D (1-3) Glucan antibody in said sample, wherein said subject is assessed as having Crohn's disease if said ACCA or said anti-polysaceharide β-D (1-3) Glucan antibody levels are elevated in said sample relative to a control reference level.

38. The method of claim 37, further comprising determining an isotype of said ALCA and said detected ACCA or said detected anti-polysaccharide β-D (1-3) Glucan antibody in said sample.

39. The method of claim 38, wherein said detected ACCA or said detected anti-polysaccharide β-D (1-3) Glucan antibody in said sample is an IgA isotype antibody.

40. The method of claim 38, wherein said ALCA and said detected ACCA or said detected anti-polysaccharide β-D (1-3) Glucan antibody in said sample is an IgG isotype antibody.

41. The method of claim 40, wherein said method further comprises detecting a level of an anti-Glc (β) IgG antibody, an anti-Glc (β 1-3) Glc (β) IgG antibody, an anti-Glc (β 1-4) Glc (β) IgG antibody, an anti-GlcNAc (β) 6-sulfate IgG antibody, or an anti-Xylan IgG antibody in said sample, wherein said subject is assessed as having Crohn's disease if the levels of each of said detected antibodies are elevated in said sample relative to a control reference level.

42. The method of claim 23, wherein said method further comprises detecting a level of an anti-GleNAc (β 1-4) GleNAc (β) antibody (ACCA) and an anti-polysaceharide β-D (1-3) Glucan antibody in said sample, wherein said subject is assessed as having Crohn's disease if said ACCA and said anti-polysaccharide β-D (1-3) Glucan antibody levels are elevated in said sample relative to a control reference level.

43. The method of claim 23, further comprising determining whether said test sample has anti-neutrophil cytoplasmic antibodies (ANCA), wherein the subject is assessed as having Crohn's Disease if said ANCA are absent from said sample.

44. The method of claim 23, further comprising detecting a level of anti-Mannan antibody (ASCA) in said sample, wherein the subject is assessed as having Crohn's disease if said ASCA is elevated in said sample relative to a control reference level.

45. The method of claim 44, further comprising determining whether said test sample has anti-neutrophil cytoplasmic antibodies (ANCA), wherein the subject is assessed as having Crohn's Disease if said ANCA are absent from said sample.

46. The method of claim 23, wherein said test sample is a biological fluid.

47. The method of claim 46, wherein said biological fluid is whole blood, serum, plasma, urine, or saliva.

48. The method of claim 46, wherein said biological fluid is serum.

49. The method of claim 23, wherein said method further comprises detecting a level of said anti-Glc (β 1-3) Glc (β) antibody (ALCA), and one, two, or three of anti-Man (α 1-3) Man (α) antibody, anti-Man (α 1-3)[Man (α 1-6)] Man (α) antibody, anti-Man (α 1-2) Man (α) antibody, anti-Man (α 1-6) Man (α) antibody (AMCA) or an anti-Mannan antibody (ASCA ) in said sample, wherein said subject is assessed as having Crohn's disease if the levels of each of said detected antibodies are elevated in said sample relative to a control reference level.

50. A method of differentially diagnosing Crohn's disease or inflammatory bowel disease in a subject with digestive symptoms of Crohn's disease or inflammatory bowel disease, the method comprising
providing a test sample from the subject;
detecting a level of an anti-neutrophil cytoplasmic antibody (ANCA) in said sample;
detecting a level of an IgG anti-Glc (β 1-3) Glc (β) antibody (ALCA) in said sample by binding of said ALCA in said sample to a carbohydrate reagent comprising an isolated Glc (β 1-3) Glc (β) glycan;
the method further comprising identifying a specific anti-Mannan antibody (ASCA) selected from the group consisting of
IgG ASCA and
IgA ASCA,
wherein absence of ANCA and presence of at least one of said IgG ALCA IgG ASCA, or IgA ASCA antibodies in said test sample indicates the subject has Crohn's disease, and
wherein the subject is assessed as having inflammatory bowel disease if ANCA is present and at least one of said IgG ALCA, IgC ASCA, IgA ASCA antibodies are present in said test sample.

51. A method of diagnosing Crohn's disease in a subject, the method comprising providing a test sample from a subject with digestive symptoms of Crohn's disease;
detecting a level of an anti-GlcNAc (β 1-4) GlcNAc (β) antibody (ACCA) in said sample by binding of said ACCA in said sample to an isolated GlcNAc (β 1-4) GlcNAc (β) on a solid phase;
detecting a level of an anti-Glc (β 1-3) Glc (β) antibody (ALCA) in said sample by binding of said ALCA in said sample to an isolated Glc (β 1-3) Glc (β) on a solid phase;
detecting a level of an anti-mannan antibody (ASCA) in said sample by binding of said ASCA in said sample to an isolated mannan on a solid phase; and
detecting a level of an anti-Man(α1,3)Man(α) antibody (AMCA) in said sample by binding of said AMCA in said sample to an isolated Man(α1,3)Man(α) on a solid phase;
wherein elevated levels of at least two of said antibodies in said test sample relative to control reference levels indicate the subject has Crohn's disease.

52. The method of claim 51, wherein elevated levels of at least three of said antibodies in said test sample relative to control reference levels indicate the subject has Crohn's disease.

53. The method of claim 51, wherein said GlcNAc (β 1-4) GlcNAc (β) glyean, said Glc(β 1-3) Glc (β), said mannan, and said Man(α 1-3)Man (α)are attached via a linker to said solid phase.

54. The method of claim 51, wherein said GlcNAc (β 1-4) GlcNAc (β), said Glc(β 1-3) Glc (β), said mannan, and said Man(α1,3)Man(α) are covalently attached to said solid phase.

* * * * *

UNITED STATES PATENT AND TRADEMARK OFFICE
CERTIFICATE OF CORRECTION

PATENT NO. : 7,592,150 B2
APPLICATION NO. : 10/728227
DATED : September 22, 2009
INVENTOR(S) : Nir Dotan et al.

It is certified that error appears in the above-identified patent and that said Letters Patent is hereby corrected as shown below:

Column 27, Line 12, Claim 10, "can antibody in said sample is an IgC isotype antibody." should read -- can antibody in said sample is an IgG isotype antibody. --

Column 27, Lines 25-26, Claim 12, "as having Crohn's disease if said ALCA and said polvsaccharide (β 1-3) Glucan antibody levels are elevated in said," should read -- as having Crohn's disease if said ALCA and said polysaccharide β-D (1-3) Glucan antibody levels are elevated in said --

Column 27, Line 62, Claim 18, "(α 1-3) [Man (α 1-6)] Man (α) antibody, anti-Man (α 1-2)," should read -- (α 1-3) Man (α) antibody, anti-Man (α 1-3)[Man (α 1-6)] Man (α) antibody, anti-Man (α 1-2) --

Column 29, Line 4, Claim 35, "detected with an enzyme-linked inununoabsorbent assay," should read -- detected with an enzyme-linked immunoabsorbent assay --

Column 29, Line 11, Claim 37, "GleNAc (β) antibody (ACCA) or an anti-polysaceharide β-D," should read -- GlcNAc (β) antibody (ACCA) or an anti-polysaccharide β-D --

Column 29, Line 14, Claim 37, "anti-polysaceharide β-D (1-3) Glucan antibody levels are," should be -- anti-polysaccharide β-D (1-3) Glucan antibody levels are --

Column 29, Lines 36-37, Claim 42, "comprises detecting a level of an anti-GleNAc (β 1-4) GleNAc (β) antibody (ACCA) and an anti-polysaceharide," should be -- comprises detecting a level of an anti-GlcNAc (β 1-4) GlcNAc (β) antibody (ACCA) and an anti-polysaccharide --

Column 30, Line 29, Claim 50, "IgG ALCA, IgC ASCA, or IgA ASCA antibodies are" should read -- IgG ALCA, IgG ASCA, or IgA ASCA antibodies are --

UNITED STATES PATENT AND TRADEMARK OFFICE
CERTIFICATE OF CORRECTION

PATENT NO. : 7,592,150 B2
APPLICATION NO. : 10/728227
DATED : September 22, 2009
INVENTOR(S) : Nir Dotan et al.

It is certified that error appears in the above-identified patent and that said Letters Patent is hereby corrected as shown below:

Column 30, Line 57, Claim 53, "GlcNAc (β) glyean, said Glc(β 1-3) Glc (β), said mannan, and" should read -- GlcNAc (β), said Glc(β 1-3) Glc (β), said mannan, and --

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,592,150 B2  Page 1 of 1
APPLICATION NO. : 10/728227
DATED : September 22, 2009
INVENTOR(S) : Dotan et al.

It is certified that error appears in the above-identified patent and that said Letters Patent is hereby corrected as shown below:

On the Title page,

Item [*] Notice: Subject to any disclaimer, the term of this patent is extended or adjusted under 35 USC 154(b) by (412) days Delete the phrase "by 412 days" and insert -- by 815 days --

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

PATENT NO.        : 7,592,150 B2                                           Page 1 of 1
APPLICATION NO.   : 10/728227
DATED             : September 22, 2009
INVENTOR(S)       : Dotan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this

Fourteenth Day of December, 2010

David J. Kappos
*Director of the United States Patent and Trademark Office*